United States Patent [19]

Wenk et al.

[11] Patent Number: 4,558,043
[45] Date of Patent: Dec. 10, 1985

[54] HETEROCYCLICAMINO CONTAINING BENZOFURANS AND 2,3-DIHYDROBENZOFURANS, COMPOSITIONS AND USE

[75] Inventors: Paul Wenk, Allschwil; Werner Breitenstein; Marcus Baumann, both of Basel, all of Switzerland

[73] Assignee: Ciba Geigy Corporation, Ardsley, N.Y.

[21] Appl. No.: 628,970

[22] Filed: Jul. 11, 1984

Related U.S. Application Data

[63] Continuation of Ser. No. 536,585, Sep. 28, 1983, abandoned.

[30] Foreign Application Priority Data

Oct. 8, 1982 [CH] Switzerland .......................... 5926/82
Apr. 22, 1983 [CH] Switzerland .......................... 2177/83

[51] Int. Cl.⁴ .................. A61K 31/535; A61K 31/54; C07D 413/02; C07D 417/02
[52] U.S. Cl. .................................. 514/210; 514/212; 514/222; 514/228; 514/232; 514/236; 514/239; 514/255; 514/320; 514/365; 514/374; 514/397; 514/411; 514/414; 514/422; 514/469; 544/58.7; 544/153; 544/376; 546/196; 548/215; 548/239; 548/146; 548/300; 548/348; 548/440; 548/454; 548/525; 260/330.9

[58] Field of Search ...................... 544/58.7, 153, 376; 546/196; 548/146, 215, 239, 300, 440, 454, 525, 348; 260/330.9; 514/210, 212, 222, 228, 232, 236, 239, 255, 320, 365, 374, 397, 411, 414, 422, 469

[56] References Cited

U.S. PATENT DOCUMENTS 2,633,468  3/1953  Pohland ............................ 546/196
4,143,055  3/1979  Occelli ............................. 424/285
4,259,338  3/1981  Paioni et al. ...................... 424/267

Primary Examiner—Robert W. Ramsuer
Attorney, Agent, or Firm—Irving N. Feit

[57] ABSTRACT

Benzofurans or 2,3-dihydrobenzofurans of the formula

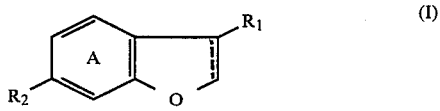

in which $R_1$ represents hydrogen or an aliphatic radical, $R_2$ represents an amino group disubstituted by a bivalent aliphatic radical which is optionally interrupted by at least one hetero atom, and the aromatic ring may be additionally substituted, and the salts thereof, have anti-inflammatory and/or analgesic activities.

22 Claims, No Drawings

HETEROCYCLICAMINO CONTAINING BENZOFURANS AND 2,3-DIHYDROBENZOFURANS, COMPOSITIONS AND USE

This application is a continuation of application Ser. No. 536,585, filed Sept. 28, 1983, now abandoned.

The invention relates to novel furans, especially optionally partially hydrogenated benzofurans, and the salts thereof, processes for the manufacture thereof, pharmaceutical preparations containing such compounds, the use of the compounds according to the invention, for example as the active ingredients of medicaments, and to processes for the manufacture of corresponding pharmaceutical preparations.

The invention relates, for example, to novel benzofurans or 2,3-dihydrobenzofurans of the formula

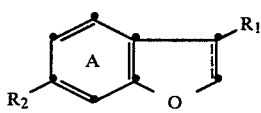

in which
$R_1$ represents hydrogen or an aliphatic radical,
$R_2$ represents an amino group disubstituted by a bivalent aliphatic radical which is optionally interrupted by at least one hetero atom,
and the aromatic ring
A may be additionally substituted,
and to the salts thereof.

The dotted line in formula I is intended to mean that there are included both benzofurans, that is to say in the furan moiety there is a double bond between the 2- and 3-positions of the ring, and 2,3-dihydrobenzofurans, that is to say the furan moiety is in the 2,3-dihydro form.

An aliphatic radical $R_1$ is especially lower alkyl, also lower alkenyl or lower alkynyl.

The amino group $R_2$ disubstituted by a bivalent aliphatic radical which is optionally interrupted by at least one hetero atom represents, for example, lower alkyleneamino or lower alkenyleneamino having one or two double bonds, each of which has, for example, from 3 up to and including 8, especially 5 or 6, ring members; lower alkyleneamino may have additionally one or two ortho-fused benzo system(s) and lower alkenyleneamino having one double bond may have additionally one ortho-fused benzo system. $R_2$ also represents, for example, lower alkyleneamino or lower alkenyleneamino having one double bond, in which the lower alkylene or lower alkenylene moiety is interrupted in each case by at least one hetero atom, especially aza, lower alkylaza, oxa or thia, especially by a hetero atom of that type, for example having from 3 up to and including 8, especially 5 or 6, ring members. In the context of $R_2$, lower alkylene or lower alkenylene is branched or, especially, unbranched and has, for example, from 2 up to and including 10, especially from 3 up to and including 6, carbon atoms. Radicals of that type are, for example, aziridin-1-yl, azetidin-1-yl, pyrrolidin-1-yl, 1-piperidyl, perhydroazepin-1-yl, indolin-1-yl, isoindolin-2-yl, carbazol-9-yl, 2- or 3-pyrrolin-1-yl, indol-1-yl, pyrrol-1-yl, imidazolidin-1-yl, oxazolidin-3-yl, thiazolidin-3-yl, piperazin-1-yl, morpholin-4-yl, thiomorpholin-4-yl, 2-imidazolin-1-yl, 4-oxazolin-3-yl and 4-thiazolin-3-yl.

The aromatic ring A may be additionally mono- or poly-substituted, for example, by an aliphatic radical, such as lower alkyl, hydroxy-lower alkyl, halo-lower alkyl, lower alkenyl or alkylene bridging 2 adjacent carbon atoms, such as lower alkylene, for example having 3 or 4 chain members, lower alkoxy, lower alkylthio, lower alkanesulphinyl, lower alkanesulphonyl, hydroxy, halogen, lower alkanoyloxy, lower alkanoyl and/or by nitro or, except for $R_2$, may be unsubstituted.

Salts of the compounds according to the invention having salt-forming groups are preferably pharmaceutically acceptable salts, such as pharmaceutically acceptable addition salts. These are formed, for example, with strong inorganic acids, such as mineral acids, for example hydrohalic acids, with strong organic carboxylic acids, such as lower alkanecarboxylic acids, optionally unsaturated dicarboxylic acids or hydroxycarboxylic acids, or with sulphonic acids, such as lower alkane- or optionally substituted benzenesulphonic acids. Acid addition salts of that type are generally formed only with those compounds of the formula I that have a basic amino group $R_2$. Salts that are unsuitable for pharmaceutical uses are also included since the latter can be used, for example, for the isolation or purification of free compounds according to the invention and the pharmaceutically acceptable salts thereof.

The general definitions used hereinbefore and hereinafter have, unless defined otherwise, especially the following meanings.

The term "lower" is to be understood as meaning that correspondingly designated organic groups or compounds contain preferably up to and including 7, especially up to and including 4, carbon atoms.

Lower alkyl is, for example, methyl, ethyl, n-propyl, isopropyl, n-butyl, isobutyl, sec.-butyl or tert.-butyl and also includes corresponding pentyl, hexyl or heptyl radicals, while lower alkenyl represents, for example, vinyl, allyl or methallyl, and lower alkynyl represents, for example, propargyl.

As substituent of the amino group $R_2$, lower alkylene is, for example, ethylene, 1,3-propylene, 1,4-butylene, 2,3-dimethyl-1,4-butylene, 1,5-pentylene or 2,5-hexylene, while corresponding lower alkenylene is, for example, 1,4-but-1-enylene or 1,4-but-2-enylene and lower alkadienylene is, for example, 1,4-buta-1,3-dienylene.

Hydroxy-lower alkyl is, for example, hydroxymethyl or 2-hydroxyethyl.

Halo-lower alkyl is, for example, chloromethyl, trifluoromethyl or 1,1,2-trifluoro-2-chloroethyl.

Lower alkylene bridging two adjacent carbon atoms and having 3 or 4 chain members has, for example, from 3 up to and including 10, especially from 3 up to and including 8, more especially 3 or 4, carbon atoms and represents, for example, 1,3-propylene or 1,4-butylene.

Lower alkoxy is, for example, methoxy, ethoxy, n-propoxy, isopropoxy, n-butoxy, isobutoxy, sec.-butoxy or tert.-butoxy.

Lower alkylthio is, for example, methyl-, ethyl-, n-propyl-, isopropyl-, n-butyl-, isobutyl-, sec.-butyl- or tert.-butyl-thio.

Lower alkane-sulphinyl or -sulphonyl is, for example, methane-, ethane-, n-propane- or isopropane-sulphinyl or -sulphonyl.

Halogen is, for example, halogen having an atomic number of up to and including 35, such as fluorine, chlorine or bromine, and includes also iodine.

Lower alkanoyloxy is, for example, acetoxy, propionyloxy, butyryloxy, isobutyryloxy or pivaloyloxy, while lower alkanoyl represents, for example, formyl, acetyl, propionyl, butyryl, isobutyryl or pivaolyl.

The compounds according to the invention have valuable pharmacological properties. They have, especially, a pronounced anti-inflammatory action which can be demonstrated, for example, by reduction of the carrageenin-induced paw oedema in rats at a dose of approximately 0.1 mg/kg p.o. and above analogously to the method described by Pasquale et al., Agents and Actions, 5, 256, (1975), and in the adjuvant-arthritis model in rats at a dose of approximately 1 mg/kg p.o. and above analogously to the method described by L. Risterer et al., Pharmacology, 2, 288 (1969). In addition, compounds of the formula I inhibit, in vitro, at a concentration of approximately 10 µmol/liter and above prostaglandin synthesis from arachidonic acid analogously to the method described by H. L. White et al., Prostaglandins, 7, 123 (1974).

The compounds according to the invention also have a distinct antinociceptive activity that can be deduced, for example, from the reduction, described by L. C. Hendershot et al., J. Pharmacol. exp. Therap. 125, 237 (1959), of the phenyl-p-benzoquinone-induced writing syndrome in mice at a dose of approximately 0.1 mg/kg p.o. and above.

Consequently, the active ingredients according to the invention can be used as anti-inflammatory agents and/or (peripheral) analgesics.

The invention relates especially to compounds of the formula I in which $R_1$ represents hydrogen, lower alkyl, lower alkenyl or lower alkynyl, $R_2$ represents lower alkyleneamino which may additionally have one or two ortho-fused benzo system(s), lower alkenyleneamino having one or two double bonds, wherein lower alkenyleneamino having one double bond may additionally have one ortho-fused benzo system, or lower alkyleneamino or lower alkenyleneamino having one double bond, each of which is interrupted in the lower alkylene or lower alkenylene moiety by at least one aza, lower alkylaza, oxa or thia group, for example having, in each case, from 3 up to and including 8 ring members and from 2 up to and including 10 carbon atoms, and the aromatic ring A is additionally mono- or poly-substituted by lower alkyl, hydroxy-lower alkyl, halo-lower alkyl, lower alkenyl, alkylene bridging two adjacent carbon atoms and having 3 or 4 chain members, lower alkoxy, lower alkylthio, lower alkanesulphinyl, lower alkanesulphonyl, hydroxy, halogen, lower alkanoyloxy, lower alkanoyl and/or by nitro or, except for $R_2$, is unsubstituted, and the salts thereof.

The invention relates more especially to compounds of the formula I in which $R_1$ represents hydrogen or lower alkyl, $R_2$ represents lower alkyleneamino which may additionally have one or two ortho-fused benzo system(s), lower alkenyleneamino having one or two double bonds, wherein lower alkenyleneamino having one double bond may additionally have one ortho-fused benzo system, each of which has from 3 up to and including 7 ring members, or lower alkyleneamino having 5 or 6 ring members or lower alkenyleneamino having one double bond and 5 ring members, each of which is interrupted in the lower alkylene or lower alkenylene moiety by an aza, lower alkylaza, oxa or thia group, and the aromatic ring A is additionally mono- or poly-substituted by lower alkyl, hydroxy-lower alkyl, halo-lower alkyl, lower alkenyl, lower alkylene bridging two adjacent carbon atoms and having 3 or 4 chain members, lower alkoxy, lower alkylthio, lower alkanesulphinyl, lower alkanesulphonyl, hydroxy, halogen, lower alkanoyloxy, lower alkanoyl and/or by nitro or, except for $R_2$, is unsubstituted, and the salts thereof.

The invention relates especially to compounds of the formula

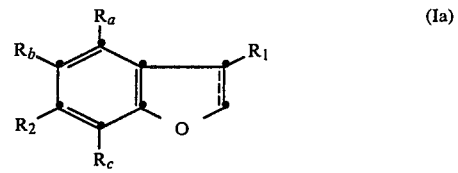

(Ia)

in which $R_1$ represents hydrogen or lower alkyl, $R_2$ represents, in each case 5- to 8-membered lower alkyleneamino, lower alkenyleneamino, aza-lower alkyleneamino, N'-lower alkylaza-lower alkyleneamino, aza-lower alkenyleneamino, N'-lower alkylaza-lower alkenyleneamino, oxa- or thia-lower alkyleneamino, isoindol-2-yl, isoindolin-2-yl, indolin-1-yl or indol-1-yl, and $R_a$, $R_b$ and $R_c$ each represents, independently of the others, hydrogen, lower alkyl, hydroxy-lower alkyl, halo-lower alkyl, lower alkenyl, lower alkoxy, lower alkylthio, lower alkanesulphinyl, lower alkanesulphonyl, hydroxy, halogen, lower alkanoyloxy, lower alkanoyl or nitro, or $R_a$ together with $R_b$ represents 3- or 4-membered alkylene and $R_c$ has the meanings given above for $R_c$, and the salts thereof.

The invention relates more especially to compounds of the formula Ia in which $R_1$ represents hydrogen or lower alkyl, for example having up to and including 4 carbon atoms, such as methyl, $R_2$ represents lower alkyleneamino having 5 or 6 ring members and from 4 up to and including 10 carbon atoms, for example pyrrolidin-1-yl or 1-piperidyl, lower alkenyleneamino having one or two double bonds and 5 or 6 ring members and from 4 up to and including 10 carbon atoms, such as 2- or 3-pyrrolin-1-yl or pyrrol-1-yl, or 4-oxa-lower alkyleneamino having 6 ring members and from 4 up to and including 10 carbon atoms, for example morpholin-4-yl, and $R_a$ and $R_c$ each represents hydrogen and $R_b$ represents hydrogen or lower alkyl, hydroxy-lower alkyl, halo-lower alkyl, lower alkoxy or lower alkylthio, for example each having up to and including 4 carbon atoms, such as methyl, hydroxymethyl, trifluoromethyl, methoxy or methylthio, hydroxy, halogen, for example having an atomic number of up to and including 35, such as chlorine, or lower alkanoyloxy, for example having from 2 up to and including 5 carbon atoms, such as pivaloyloxy, or $R_a$ and $R_b$ together represent lower alkylene having 3 or 4 chain members, for example having 3 or 4 carbon atoms, such as 1,4-butylene, and $R_c$ is hydrogen, and the salts thereof.

The invention relates more especially to compounds of the formula Ia in which $R_1$ represents hydrogen or lower alkyl having up to and including 4 carbon atoms, such as methyl, $R_2$ represents 1-pyrrolyl, 4-morpholinyl, 3-pyrrolin-1-yl or unbranched 4- to 6-membered alkyleneamino, $R_a$ and $R_c$ each represents hydrogen and $R_b$ represents hydrogen, lower alkyl having up to and including 4 carbon atoms or halogen having an atomic number of up to and including 35, such as methyl or chlorine, or $R_c$ represents hydrogen and $R_a$ and $R_b$ together represent 3- or 4-membered alkylene, or one of the radicals $R_a$ and $R_b$ represents halogen having an atomic number of up to and including 35 and the other represents lower alkyl having up to 4 carbon atoms, such as chlorine or methyl, and the salts thereof.

The invention relates especially to, on the one hand, compounds of the formula

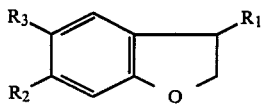

(Ib)

or, on the other hand, to compounds of the formula

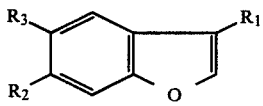

(Ic)

in which, in each case, $R_1$ represents hydrogen or lower alkyl having up to and including 4 carbon atoms, such as methyl, $R_2$ represents pyrrolidin-1-yl, 1-piperidyl, pyrrol-1-yl or morpholin-4-yl and $R_3$ represents hydrogen, lower alkyl having up to and including 4 carbon atoms, such as methyl, or halogen having an atomic number of up to and including 35, such as chlorine, and the salts thereof.

The invention relates especially to compounds of the formula Ic in which $R_1$ represents hydrogen or lower alkyl having up to and including 4 carbon atoms, especially methyl, $R_2$ represents pyrrol-1-yl and $R_3$ represents lower alkyl having up to and including 4 carbon atoms, especially methyl.

The invention relates especially to the novel compounds mentioned in the Examples and to the salts thereof.

The compounds according to the invention and salts of those compounds having salt-forming properties can be manufactured, for example, in a manner known per se, for example by (a) in a compound of the formula

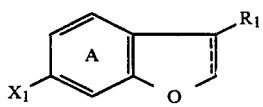

(II)

in which $X_1$ is a radical that can be converted into $R_2$ or can be replaced by $R_2$, converting $X_1$ into $R_2$ or replacing $X_1$ by $R_2$, or (b) for the manufacture of 2,3-dihydrobenzofurans of the formula I, in a compound of the formula

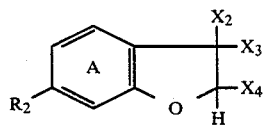

(III)

in which $X_2$ is $R_1$ and one of the radicals $X_3$ and $X_4$ represents a radical that can be replaced by hydrogen and the other is hydrogen, or $X_3$ and $X_4$ together represent an additional bond, replacing $X_3$ or $X_4$ by hydrogen or reducing the additional bond represented by $X_3$ and $X_4$ or, if $R_1$ is hydrogen, $X_2$ and $X_3$ together represent a bivalent group that can be replaced by 2 hydrogen atoms and $X_4$ is hydrogen, replacing $X_2$ and $X_3$ by 1 hydrogen atom in each case, or (c) for the manufacture or benzofurans or 2,3-dihydrobenzofurans of the formula I in which $R_1$ represents an aliphatic radical, introducing the radical $R_1$ into a compound of the formula

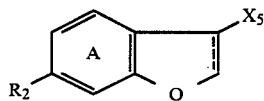

(IVa)

by reaction with a compound of the formula $R_1$—$X_5'$ (IVb), in which one of the radicals $X_5$ and $X_5'$ represents optionally reactive, esterified or etherified hydroxy and the other represents a metallic radical, or in which $X_5$ and $X_5'$ each represents halogen, and with removal of $X_5$—$X_5'$, or (d) cyclising a compound of the formula

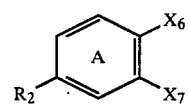

(V)

in which $X_6$ represents a group of the formula —CH($R_1$)—CH$_2$—$X_6'$ wherein $X_6'$ represents a removable radical, and $X_7$ is hydroxy, or in which, if $R_1$ in the formula I represents an aliphatic radical, $X_6$ represents a diazonium group or halogen and $X_7$ represents a group of the formula —O—CH$_2$—CH=$R_1'$, wherein $R_1'$ is a double-bonded aliphatic radical corresponding to the radical $R_1$, to form a 2,3-dihydrobenzofuran compound of the formula I, or cyclising a compound of the formula V in which $X_6$ is hydrogen and $X_7$ represents a group of the formula —O—CH$_2$—C(=O)—$R_1$ or a derivative thereof, or in which $X_6$ represents a group of the formula —C($R_1$)=CH—$X_6''$ wherein $X_6''$ represents a removable radical, and $X_7$ is hydroxy, to form a benzofuran compound of the formula I, or (e) for the manufacture of benzofurans of the formula I, in a compound of the formula

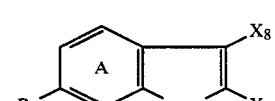

(VI)

in which one of the radicals $X_8$ and $X_9$ represents a radical that can be replaced by hydrogen and the other represents hydrogen or, in the case of $X_8$, a radical $R_1$ other than hydrogen, replacing $X_8$ or $X_9$ by hydrogen, or (f) for the manufacture of benzofurans of the formula I, removing the grouping $X_{10}$–$X_{11}$ from a compound of the formula

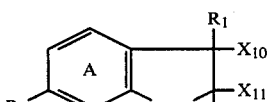

(VII)

in which one of the radicals $X_{10}$ and $X_{11}$ represents a removable radical and the other is hydrogen, or in which $X_{10}$ and $X_{11}$ each represents halogen, carboxy or hydrogen, with the formation of an additional bond, or (g) for the manufacture of benzofurans of the formula I in which $R_1$ represents an aliphatic radical, isomerising a compound of the formula

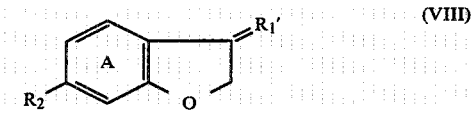

in which $R_1'$ represents a double-bonded aliphatic radical that corresponds to the radical $R_1$ and is other than hydrogen, and, if desired, converting a resulting compound according to the invention into a different compound according to the invention and/or, if desired, converting a resulting salt into the free compound and/or, if desired, converting a resulting compound according to the invention having salt-forming properties into a salt and/or, if desired, separating a resulting mixture of isomers into the individual isomers.

The invention relates also to the compounds that can be obtained according to the processes described above.

Unless stated otherwise, the reactions described hereinbefore and hereinafter in the variants (a)–(g) are carried out in a manner known per se, in the absence, or customarily in the presence, of a suitable solvent or diluent or a mixture thereof, with cooling, at room temperature or with heating, for example within a temperature range of from approximately $-10°$ C. to approximately $250°$ C., preferably from approximately $40°$ C. to approximately $150°$ C., and, if necessary, in a closed vessel, optionally under pressure, in an inert gas atmosphere and/or under anhydrous conditions.

The starting materials mentioned hereinbefore and hereinafter of the formulae II, III, IVa, IVb, V, VI, VII and VIII can also be manufactured according to methods known per se.

Variant (a):

A radical $X_1$ can be converted into $R_2$ represents, for example, an amino group or a group of the formula —NH—alk—$Z_1$ in which alk represents a bivalent aliphatic radical that is optionally interrupted by at least one hetero atom and corresponds to the radical $R_2$ and $Z_1$ represents optionally reactive hydroxy, especially hydroxy esterified, for example, by a mineral acid or a sulphonic acid, or by a carboxylic acid. Accordingly, $Z_1$ may represent, for example, halogen, such as chlorine or bromine, sulphato or optionally substituted phenyl- or lower alkane-sulphonyloxy, such as p-toluene-, p-bromophenyl-, methane- or trifluoromethane-sulphonyloxy, also optionally substituted lower alkanoyloxy, such as acetoxy or trifluoroacetoxy.

The conversion of $X_1$ into $R_2$ is customarily carried out in the presence of a condensation agent, such as an acid or, especially, a base. There come into consideration as acids, for example, strong protonic acids, such as mineral acids, for example sulphuric acid or a phosphoric acid, or sulphonic acids, for example p-toluenesulphonic acid, while suitable bases are, for example, alkali metal hydroxides, for example sodium hydroxide, alkali metal lower alkoxides, such as sodium methoxide, tertiary nitrogen bases, optionally cyclic, for example triethylamine, ethyldiisopropylamine, piperidine, collidine, 1,5-diazabicyclo[4.3.0]non-5-ene (DBN) or 1,8-diazabicyclo[5.4.0]undec-7-ene (DBU), also lithium di-lower alkylamides, for example lithium diethylamide or lithium diisopropylamide.

In a further embodiment for the manufacture of compounds of the formula I in which $R_2$ represents morpholin-4-yl or thiomorpholin-4-yl, there is used, for example, a starting material of the formula II in which $X_1$ represents a group of the formula —N(CH$_2$—CH$_2$—OH)$_2$ or —N(CH$_2$—CH$_2$—SH)$_2$, respectively, which is condensed, for example, in the presence of a strong protonic acid, such as sulphuric acid. Compounds of the formula I in which $R_2$ represents morpholin-4-yl or thiomorpholin-4-yl can be obtained also by reacting a starting material of the formula II in which $X_1$ is amino, for example, with a 2,2'-dihalodiethyl(thio)ether, such as 2,2'-dibromodiethyl(thio)ether, in the presence of a basic condensation agent, for example one of those mentioned above, such as N-ethyldiisopropylamine. In that operation, there is formed intermediately a compound of the formula II in which $X_1$ represents a group of the formula —NH—C$_2$H$_4$—O—C$_2$H$_4$—Hal or the corresponding thio form. Advantageously, starting compounds of that type are not isolated, but are further condensed under corresponding reaction conditions.

For the manufacture of compounds of the formula I in which $R_2$ represents pyrrol-1-yl, there are used especially starting compounds of the formula II in which $X_1$ represents amino and these compounds are reacted, for example, with 2,5-di-lower alkoxytetrahydrofuran, such as 2,5-dimethoxytetrahydrofuran, a 4-lower alkoxy-, such as 4-methoxy-, but-3-en-1-yne, or with an optionally acetalised succinic dialdehyde or the tautomeric enol form thereof.

If $X_1$ represents, for example, halogen, such as chlorine, bromine or iodine, and if in the orthoposition to $X_1$ there is at least one substituent having a strong —I or —M effect, such as halogen, nitro or trifluoromethyl, then $X_1$ can be replaced by $R_2$. The replacement can be carried out, for example, by reaction with a compound of the formula $R_2$—H or $R_2$—Me, wherein $R_2$ represents a basic amino group disubstituted by a bivalent aliphatic radical which is optionally interrupted by at least one hetero atom and Me represents a metallic radical, such as an alkali metal, for example lithium. In isolated cases, it is advantageous to carry out these reactions under pressure and/or at elevated temperatures. Advantageously the amines are used in excess.

For the manufacture of benzofurans of the formula II in which $X_1$ represents an amino group or a group of the formula —NH—alk—$Z_1$, there is used as starting material, for example, a 3-nitrophenol which is reacted, for example, with a compound of the formula $R_1$—CO—CH$_2$—Hal in which Hal represents halogen, or a corresponding acetal thereof, for example chloroacetone or 2-chloro-1,1-diethoxyethane, in the presence of a base, for example potassium carbonate, with heating, to form a compound of the formula

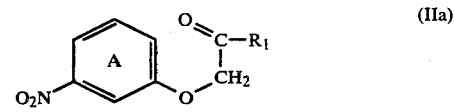

or an acetal thereof. After reduction of the nitro group, for example by hydrogenation in the presence of a hydrogenation catalyst, such as Raney nickel, the resulting amino compound can be cyclised, for example, using an acid condensation agent, such as concentrated sulphuric acid, to form the corresponding compound of the formula II in which $X_1$ represents amino, which compound can, if desired, be converted, for example by reaction with not more than one mole of a compound of the formula $Z_1$—alk—$Z_1$, into a compound of the formula II in which $X_1$ represents a group of the formula —NH—alk—$Z_1$. The manufacture of starting compounds of the formula II in which $X_1$ represents halogen can be carried out in analogous manner, starting, for example, from a 3-halophenol, via condensation with a compound of the formula $R_1$—CO—$CH_2$—Hal, or an acetal thereof, and cyclisation.

2,3-dihydrobenzofurans of the formula II can be obtained, for example, by acylating, for example, a 3-halo-1-lower alkoxybenzene derivative with an acetyl halide in the presence of a Lewis acid, for example aluminium chloride. In that operation, the lower alkyl ether can simultaneously be cleaved to form the corresponding phenol. The latter is advantageously etherified again in customary manner. In the next reaction step, for example, the acetophenone derivative is reacted analogously to the Willgerodt for Kindler reaction, for example with sulphur and morpholine, and, for example, the resulting thiomorpholide is converted by treatment with an acid into a compound of the formula

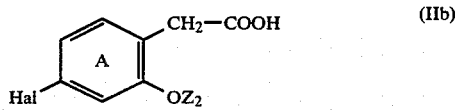
(IIb)

in which $Z_2$ is lower alkyl. By reaction with a halide of the formula $R_1$—Hal in the presence of a strong base, for example sodium amide, a radical $R_1$ other than hydrogen can be introduced. Subsequent reduction of the carboxy group using a hydride-transferring reagent, for example lithium aluminium hydride, results, for example, in compounds of the formula

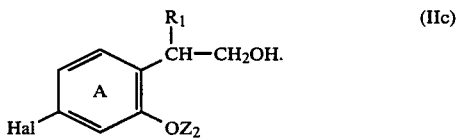
(IIc)

By reaction with a Lewis acid, for example boron tribromide, using corresponding proportions, the ether can be cleaved and the hydroxy group can be substituted by the corresponding halogen atom. In the subsequent reaction step, cyclisation to form 2,3-dihydrobenzofurans of the formula II in which $X_1$ represents halogen is carried out by condensation using a base, such as 1,8-diazabicyclo[5.4.0]undec-7-ene. For the manufacture of corresponding amino compounds of the formula II ($X_1$=amino), there are used as starting materials, for example, 1-lower alkoxy-3-nitrobenzene compounds and the reaction sequence is carried out in analogous manner, in the course of which the nitro group may be reduced to form the amino group which, for its part, may, if desired, be temporarily protected, for example by acylation.

Variant (b):

A radical $X_3$ or $X_4$ that can be replaced by hydrogen represents, for example, hydroxy, esterified hydroxy, for example hydroxy esterified by a mineral acid, sulphonic acid or organic carboxylic acid, etherified hydroxy, substituted thio or seleno or disubstituted amino. There may be mentioned as examples of radicals of that type: halogen, such as chlorine or bromine, optionally substituted phenyl- or lower alkane-sulphonyloxy, such as p-toluene-, p-bromophenyl-, methane- or trifluoromethane-sulphonyloxy, lower alkoxy, optionally substituted phenyl- or lower alkyl-thio or -seleno, such as phenyl- or methyl-thio or -seleno, di-lower alkylamino, such as dimethylamino, disulphonyloxyamino, such as ditoluenesulphonyloxyamino, or lower alkanoyloxy, such as acetoxy.

The reductive replacement of $X_3$ or $X_4$ by hydrogen is carried out in a manner known per se, for example by hydrogenation in the presence of a hydrogenation catalyst, by reduction with a hydride-transferring reagent or by a metallic reduction system comprising a metal and a proton-removing agent.

There may be mentioned as hydrogenation catalysts, for example, elements of sub-group VIII of the Periodic Table of elements, or derivatives thereof, such as palladium, platinum, platinum oxide, cobalt, Raney nickel, rhodium or tris(triphenylphosphine)rhodium(I) halide, for example chloride, which may, if desired, be supported on a suitable carrier, such as active carbon, an alkaline earth metal carbonate or sulphate or silica gel. There are included amongst the hydride-transferring reagents, for example, suitable alkali metal aluminium hydrides or borohydrides or tin hydrides, such as lithium aluminium hydride, sodium borohydride, lithium triethyl borohydride, sodium cyanoborohydride or triethyltin hydride. The metal component of the metallic reduction system is, for example, a base metal, such as an alkali metal or alkaline earth metal, for example sodium, lithium, magnesium or calcium, or a transition metal, for example zinc, tin, iron or titanium, while there come into consideration as proton-removing agents, for example, protonic acids, such as hydrochloric or acetic acid, lower alkanols, for example ethanol, and/or amines or ammonia. Such systems are, for example, sodium/ammonia, zinc/hydrochloric or acetic acid or zinc/ethanol.

In preferred embodiments of this process, for example, hydroxy, hydroxy esterified by a lower alkanecarboxylic acid, substituted thio or seleno and disubstituted amino are reduced by hydrogenation with hydrogen and, for example, the following radicals are reduced by hydride-transferring reagents: halogen (for example with tributyltin hydride, lithium aluminium hydride, sodium borohydride or sodium cyanoborohydride), sulphonyloxy (for example with sodium cyanoborohydride, lithium aluminium hydride or lithium triethyl borohydride), lower alkanoyloxy (for example with lithium aluminium hydride), and disulphonyloxyamino (for example with sodium borohydride).

Preferably, benzylic radicals ($X_3$) that can be replaced by hydrogen are replaced by hydrogen by reduction.

Starting from compounds of the formula III in which the variables $X_2$ and $X_3$ represent, especially, substituted thio groups, for example those of the type mentioned above, especially lower alkylthio, $X_2$ and $X_3$ can be replaced by hydrogen, for example, in each case, by hydrogenation with hydrogen in the presence of one of the hydrogenation catalysts mentioned, especially Raney nickel, it being possible for a compound of the formula III in which $X_2$ and $X_4$ are hydrogen and $X_3$ represents correspondingly substituted thio, to be formed in situ. In compounds of the formula III in which $X_2$ $X_3$ together represent a bivalent group that can be replaced by two hydrogen atoms and $X_4$ is hydrogen, the bivalent group represents, for example, an oxo group or an optionally substituted hydrazono group.

The oxo group can be replaced directly by two hydrogen atoms, for example, analogously to the Clemmensen reduction using amalgamated zinc in the presence of a protonic acid, such as hydrochloric acid. The replacement of the oxo group can be carried out also with hydrazine in the presence of an alkali metal hydroxide, according to Wolff-Kishner, or in a high-boiling solvent, especially in a corresponding ether, at elevated temperatures, according to Huang-Minlon, or in the presence of an alkali metal alkoxide, especially potassium tert.-butoxide in dimethyl sulphoxide, according to Gram. A hydrazone ($X_2$, $X_3$ together: $=N-NH_2$) may be formed intermediately which, advantageously, is not isolated and from which nitrogen is removed under the reaction conditions.

If $X_2$ and $X_3$ together represent, for example, substituted hydrazono, such as sulphonylhydrazono, for example p-toluenesulphonylhydrazono, then this can be replaced by two hydrogen atoms, for example, using a hydride-transferring reagent, such as one of those mentioned above, especially sodium borohydride, lithium aluminium hydride or sodium cyanoborohydride.

In the course of the replacement of the radicals or groups that can be replaced by hydrogen, the elimination of H-$X_3$ or H-$X_4$ can occur as a secondary reaction. This can be repressed according to the pH-conditions. Thus, the operation can be carried out especially in a neutral medium which is obtained, for example, by suitable buffer systems. Likewise, if a starting material of the formula III is chosen in which $X_3$ and $X_4$ represent monovalent groups that can be eliminated, for example, by bases, such as esterified hydroxy, the operation can preferably be carried out in an acidic medium; in the case of the reduction of those compounds of the formula III in which the corresponding radicals that can be replaced by hydrogen are radicals that can be eliminated in a secondary reaction under acid conditions, especially hydroxy, the reduction can preferably be carried out in an alkaline medium.

A further radical $X_3$ or $X_4$ that can be replaced by hydrogen is a carboxy group. The decarboxylation of corresponding compounds of the formula III can be carried out customarily at elevated temperatures, for example at a temperature of approximately 50° C. and above, especially within a temperature range of from 100° to approximately 300° C. The decarboxylation can be assisted, for example, by the presence of bases, for example high-boiling nitrogen bases, for example collidine, and/or in the presence of noble metals, such as copper.

The reduction of the additional bond represented in compounds of the formula III by $X_3$ and $X_4$ is carried out especially by hydrogenation in the presence of one of the hydrogenation catalysts mentioned, also using a hydride-transferring reagent, for example an alkali metal borohydride, such as potassium borohydride.

In the course of the above-mentioned reduction reactions, especially in the case of hydrogenation reactions, multiple bonds which may be present, for example those in corresponding radicals $R_1$, $R_2$, and also substituents of the ring A can also be reduced.

The starting material of the formula III in which $X_2$ is $R_1$, $X_3$ represents hydroxy, or in which $X_2$ and $X_3$ together represent an oxo group, and $X_4$ is, in each case, hydrogen can be manufactured, for example, by acetylating a 3-nitrophenol with acetyl chloride in the presence of a Lewis acid, subsequently reducing the nitro group to form an amino group by hydrogenation in the presence of a hydrogenation catalyst and converting the amino group into $R_2$ according to variant (a). The compounds of the formula

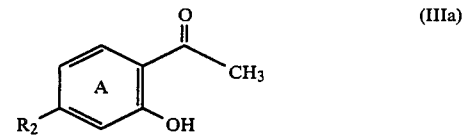

so obtained are, for example, brominated, and cyclised in the presence of a base, such as sodium acetate, to form compounds of the formula III in which $X_2$ and $X_3$ form an oxo group and $X_4$ is hydrogen. These intermediates can, on the one hand, be reacted analogously to the Grignard reaction with compounds of the formula $R_1$—Mg—Hal in which $R_1$ is other than hydrogen to form compounds of the formula III in which $X_2$ is $R_1$ other than hydrogen, $X_3$ represents hydroxy and $X_4$ is hydrogen or, on the other hand, be reduced with a hydride-transferring reagent, for example sodium borohydride, to form compounds of the formula III in which $X_2$ represents hydrogen, $X_3$ is hydroxy and $X_4$ represents hydrogen.

Further compounds of the formula III in which one of the radicals $X_3$ and $X_4$ represents a radical that can be replaced by hydrogen can be obtained, for example, starting from compounds of the formula III in which one of the radicals $X_3$ and $X_4$ represents hydroxy. The hydroxy group can, for example, be substituted by halogen by means of customary inorganic acid halides, such as phosphorus halides, phosphorus trichloride, phosphorus tribromide, phosphorus oxychloride or thionyl chloride, be esterified to form sulphonyloxy or acyloxy by treatment with a sulphonic acid or an organic carboxylic acid, or a reactive derivative thereof, or be reacted to form a substituted thio radical by reaction with a mercaptan in the presence of a Lewis acid. Halogen, in its turn, may be converted, for example, by treatment with copper(I) cyanide into cyano from which the carboxy group $X_3$, also $X_4$, can be obtained by hydrolysis. Carboxy compounds, for their part, can be converted into amino by way of a transposition reaction, for example according to Curtius, Lossen, Schmidt or Hofmann, and subsequently disubstituted, for example by customary alkylation.

The radicals $X_3$ or $X_4$ that can be replaced by hydrogen may also be introduced at an earlier stage in the reaction sequence.

Variant (c):

A reactive esterified hydroxy group $X_5$ or $X_5'$ represents, for example, a hydroxy group esterified especially by a mineral acid, more especially a hydrohalic acid, and represents especially halogen, such as chlorine, bromine or iodine, also hydroxy esterified by a sulphonic acid or an organic carboxylic acid, for example (trifluoro-)methane- or p-toluene-sulphonyloxy.

Etherified hydroxy represents especially lower alkoxy.

A metallic radical $X_5$ or $X_5'$ represents, for example, a mono- or bi-valent metal, such as an alkali metal, especially lithium, or represents a bivalent metal radical, such as a cadmium radical or, especially, a magnesium radical, for example a magnesium halide radical.

It is preferable to use those compounds of the formula IVa or IVb in which X$_5$ and X$_5'$, respectively, represent halogen.

When using alkali metal compounds, especially lithium compounds, of the formula IVa or IVb, the operation is advantageously carried out at reduced temperatures, for example within the range of from 10° C. to −78° C.

The reaction of benzofurans of the formula IVa with compounds of the formula IVb in which X$_5$ represents optionally etherified hydroxy and X$_5'$ represents an alkali metal, especially lithium, is carried out advantageously with the addition of nickel or palladium compounds, for example nickel(II) chloride.

The reaction of compounds of the formulae IVa and IVb in which X$_5$ and X$_5'$ each represents halogen may be carried out, for example, in accordance with the Wurtz or Fittig reaction, for example in the presence of an alkali metal, such as sodium.

The method of manufacture of starting materials of the formula IVa is described, for example, in connection with the manufacture of starting compounds of the formula III or VI [Variant (b) or (e)], or is carried out according to methods known per se.

Variant (d):

In a starting material of the formula V in which X$_6$ represents a group of the formula —CH(R$_1$)—CH$_2$—X$_6'$ and X$_7$ is hydroxy, the leaving group X$_6'$ represents, for example, optionally reactive, esterified hydroxy, esterified, for example, by a mineral acid, a sulphonic acid or an organic carboxylic acid, such as halogen, sulphato, optionally substituted phenyl- or lower alkane-sulphonyloxy or optionally substituted lower alkanoyloxy. There may be mentioned especially chlorine, bromine, sulphato, p-toluenesulphonyloxy and acetoxy.

The cyclisation is carried out, for example, in the presence of a condensation agent, such as one of the strong protonic acids mentioned above or, especially, one of the bases mentioned above.

Thus, for example, starting compounds of the formula V in which X$_6$ represents a group of the formula —CH(R$_1$)—CH$_2$—X$_6''$ and X$_6''$ represents halogen, such as bromine, can be cyclised in the presence of a basic condensation agent, for example DBU.

When cyclising starting compounds of the formula V in which X$_6$ represents a diazonium group and X$_7$ represents a group of the formula —O—CH$_2$—CH=R$_1'$, the operation is carried out, for example, in the presence of reducing systems, such as titanium(III) halides, for example titanium(III) chloride, or systems comprising a metal, such as an alkali metal, and a lower alkanol. If X$_6$ represents halogen, especially iodine, the cyclisation is carried out preferably in the presence of a hydride-transferring reagent, especially tributyltin hydride.

The cyclisation of compounds of the formula V in which X$_6$ is hydrogen and X$_7$ represents a group of the formula —O—CH$_2$—CO—R$_1$, can be carried out, for example, in the presence of a condensation agent, such as one of the strong protonic acids already mentioned, for example p-toluenesulphonic acid, hydrochloric acid or sulphuric acid, or a titanium(III) halide, for example titanium(III) chloride. In that operation, it is also possible to use those compounds of the formula V in which the carbonyl group of the radical X$_7$ is in derivatised, for example acetalised, form. Corresponding acetals are formed, for example, from lower alkanols or lower alkanediols or corresponding mercaptans.

A group X$_7$ of the formula —O—CH$_2$—CO—R$_1$ may also be in the corresponding tautomeric enol form (X$_7$=—O—CH=C(OH)—R$_1$).

In compounds of the formula V in which X$_6$ represents a group of the formula —C(R$_1$)=CH—X$_6''$ and X$_7$ represents hydroxy, the leaving group X$_6''$ represents, especially, lower alkoxy, but has also the meanings given for X$_6'$.

The corresponding cyclisation can be carried out, just as can the cyclisation described immediately above, in the presence of a condensation agent, especially an acidic condensation agent, advantageously using perchloric acid.

For the manufacture of a starting material of the formula V in which X$_6$ represents a group of the formula —CH(R$_1$)—CH$_2$—X$_6'$ and X$_7$ is hydroxy, for example a 1-lower alkoxy-3-nitrobenzene is used as starting material and is acylated in the presence of a Lewis acid, for example with an acetyl halide. In that operation, the ether grouping may be cleaved; more advantageously however, it is re-formed. In the 1-acetyl-2-lower alkoxy-4-nitrobenzene so obtained, the nitro group can be converted, for example, by hydrogenation in the presence of a hydrogenation catalyst into an amino group and the amino group can be converted into the radical R$_2$ analogously to Variant (a). A resulting compound of the formula

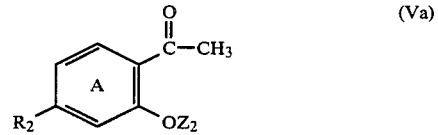

can be reacted to form the corresponding thiomorpholide in the subsequent reaction step in accordance with the Willgerodt or Kindler reaction, for example with sulphur and morpholine, which thiomorpholide is subsequently hydrolysed. If desired, a radical R$_1$ other than hydrogen can be introduced by reaction with a halide of the formula R$_1$—Hal in the presence of a strong base, such as sodium amide. Subsequently the ether is cleaved, for example by treatment with a strong hydrohalic acid or a Lewis acid, it being possible for cyclisation to form compounds of the formula

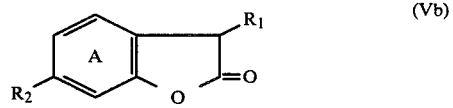

to be carried out at the same time. The lactone ring is subsequently opened, for example by treatment with a base. In resulting compounds of the formula

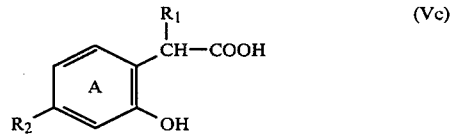

the carboxy group can be converted into the hydroxymethyl group by reduction, for example with lithium aluminium hydride. If desired, in, for example, resulting starting compounds of the formula V in which X$_6$ represents a group of the formula —CH(R$_1$)—CH$_2$—X$_6'$ and $X_6'$ is hydroxy, the hydroxy is converted into a different leaving group $X_6'$, for example into halogen, for example by reaction with a suitable halogenating reagent, such as a boron trihalide.

A starting material of the formula V in which $X_6$ represents a diazonium group or halogen and $X_7$ represents a group of the formula —O—CH$_2$—CH=R$_1'$ can be obtained, for example, by introducing the radical R$_2$ into a 3-aminophenol analogously to Variant (a), nitrating the resulting compound of the formula

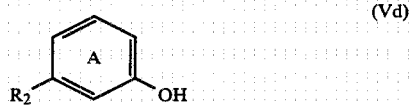
(Vd)

and converting the nitro group into an amino group by reduction, for example with iron in hydrochloric acid or by hydrogenation in the presence of a hydrogenation catalyst. Reaction with a compound of the formula Hal—CH=CH—R$_1$ in the presence of a base may result, for example, in compounds of the formula

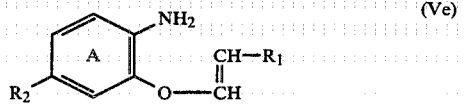
(Ve)

or isomers thereof. The amino group is subsequently diazotised, for example with nitrous acid, and, if desired, the diazonium group is treated, for example, analogously to the Sandmeyer reaction with a copper(I) halide and thus replaced by a halogen atom.

For the manufacture of starting compounds of the formula V in which $X_6$ is hydrogen and $X_7$ represents a group of the formula —O—CH$_2$—CO—R$_1$, there is used as starting material, for example, a compound of the formula Vd and this is reacted, for example, with a compound of the formula Hal—CH$_2$—CO—R$_1$.

A starting material of the formula V in which $X_6$ represents a group of the formula —C(R$_1$)=CH—X$_6''$ and $X_6''$ and $X_7$ are hydroxy can be obtained, for example, by converting, for example, a compound of the formula Vc into the carboxylic acid halide, for example with oxalyl chloride, and converting the halocarbonyl group into the formyl group, which is in equilibrium with the tautomeric enol group, for example according to Rosenmund, by hydrogenation in the presence of palladium on barium sulphate, or using lithium tri-tert.-butoxyaluminium hydride, at low temperatures.

Variant (e):

In compounds of the formula (VI), the radicals $X_8$ and $X_9$ that can be replaced by hydrogen can have, for example, the meanings given in Variant (b) for $X_3$ and $X_4$. They represent especially, however, hydroxy, esterified hydroxy or substituted thio, and, more especially, carboxy. Correspondingly, radicals of that type can be replaced by hydrogen, for example as given in Variant (b). Preferably, corresponding radicals other than carboxy are in the 3-position of the ring system and carboxy is, especially, in the 2-position.

Compounds of the formula VI in which $X_8$ represents carboxy and $X_9$ is hydrogen can be obtained, for example, by reacting, for example, a compound of the formula Vd in the presence of a base firstly with a compound of the formula Hal—CH$_2$—COOZ$_2$ and then with an oxalic acid diester. After hydrolysis of the ester groups and cyclisation using a strong protonic acid, resulting compounds of the formula

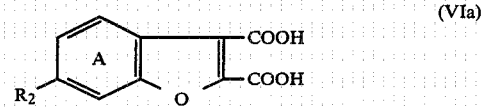
(VIa)

can be decarboxylated in customary manner to form the corresponding compounds of the formula VI in which $X_8$ represents carboxy and $X_9$ is hydrogen.

Starting compounds of the formula VI in which $X_8$ is hydrogen and $X_9$ represents carboxy can be obtained, for example, by reacting a compound of the formula

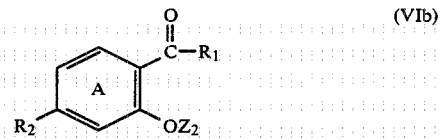
(VIb)

in which $Z_2$ is hydrogen with an ester of the formula Hal—CH(COOH)$_2$ in the presence of a base and while heating, and hydrolysing the resulting compound of the formula

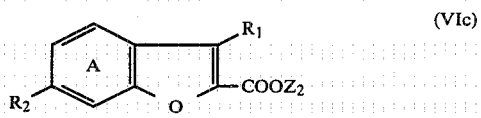
(VIc)

in which $Z_2$ represents, for example, lower alkyl, with formation of the free acid.

Variant (f):

Removable radicals $X_{10}$ and $X_{11}$ in compounds of the formula VII are, for example, hydroxy optionally esterified, for example, by a mineral acid, such as hydrohalic or sulphuric acid, sulphonic acids, such as optionally substituted phenyl- or lower alkanesulphonic acids, or by organic carboxylic acids, such as optionally substituted lower alkanecarboxylic acids, etherified hydroxy, such as lower alkoxy, disubstituted sulphonium, such as di-lower alkylsulphonium, trisubstituted ammonium, such as tri-lower alkylammonium, substituted sulphinyl, such as optionally substituted phenyl- or lower alkanesulphinyl, disubstituted N-oxidoamino, such as di-lower alkyl-N-oxidoamino, or lower alkylthiothiocarbonyloxy.

The elimination of $X_{10}$–$X_{11}$ from corresponding compounds of the formula VII can be carried out, for example, in the presence of a protonic acid, a Lewis acid, or acidic inorganic salts ($X_{10}$ or $X_{11}$=hydroxy), in the presence of a base ($X_{10}$ or $X_{11}$=esterified or etherified hydroxy, disubstituted sulphonium or trisubstituted ammonium), or thermally ($X_{10}$ or $X_{11}$=substituted sulphinyl, disubstituted N-oxidoamino or lower alkylthiothiocarbonyloxy). There come into consideration as acids or bases especially those of the type mentioned above, and as bases also lithium di-lower alkylamides, such as lithium diethylamide or lithium dipropylamide. The thermal elimination is carried out, for example, within a temperature range of from approximately 50° to approximately 300° C.

If $X_{10}$ and $X_{11}$ of the formula VII each represents hydrogen, a molecule of hydrogen can be removed with the formation of an additional bond, for example, in the presence of a dehydrogenation agent. Such dehydrogenation agents are, for example, hydrogenation catalysts, for example those of the type mentioned above, which may optionally be supported on a suitable carrier, for example quinones, such as p-benzoquinones, for example tetrachloro-p-benzoquinone or 2,3-dichloro-5,6-dicyano-p-benzoquinone, anthraquinones or phenanthren-9,10-quinone. It is also possible to use selenium or selenium derivatives, such as selenium dioxide or diphenylselenium bis-trifluoroacetate.

If $X_{10}$ and $X_{11}$ of the formula VII each represents halogen, such as chlorine, bromine or iodine, a molecule of halogen can be removed with formation of an additional bond, for example, under reductive conditions, such as in the presence of base metals, such as zinc or magnesium, or metal-organic reduction systems, such as alkaline metal salts of dimethylsulfoxide, or sodium iodide, for example in acetone.

If $X_{10}$ and $X_{11}$ of the formula VII each represents carboxy, the double bond may be introduced, for example, by oxidation with a suitable oxidizing agent, such as lead (IV) acetate, for example, in the presence of a base, such as piperidine.

The starting compounds of the formula VII or the precursors thereof can be manufactured, for example, analogously to the manufacture of compounds of the formula III (Variant b).

Variant (g):

Intermediate compounds of the formula VIII are formed in customary manner in situ and can be isomerised to form corresponding compounds of the formula I, for example under the reaction conditions for their manufacture. If the compounds of the formula VIII are isolated, they can be isomerised, for example, in the presence of a base or an acid or thermally. This isomerisation can also be carried out in the presence of suitable rhodium compounds, such as rhodium(III) halides, for example rhodium trichloride.

The formation of intermediate compounds of the formula VIII can be carried out, for example, starting from compounds of the formula III in which $X_2$ and $X_3$ together represent an oxo group and $X_4$ is hydrogen, by reacting such compounds, for example, analogously to the Wittig reaction or the Horner variant, with compounds of the formula $(C_6H_5)_3P=R_1'$ or $(Z_2O)_2P-(=O)-R_1'$, wherein $R_1'$ represents a double-bonded aliphatic radical corresponding to the radical $R_1$ and $Z_2$ represents, for example, lower alkyl.

The intermediates of the formula VIII can also be formed, for example, by reacting a compound of the formula III in which $X_2$ and $X_4$ represent hydrogen and $X_3$ is halogen, especially bromine, firstly, on the one hand, with triphenylphosphine or, on the other hand, with a phosphorous acid ester of the formula $(Z_2O)_3$-$P=O$ and subsequently converting them into the alkylidene phosphorane or the phosphorous acid ester respectively, using, in each case, a strong base, such as n-butyllithium, sodium amide or sodium methylsulphinylmethanide. In the next reaction step, these reactive organophosphoric compounds are reacted with an aldehyde of the formula $R_1''$—CHO in which $R_1''$ represents an aliphatic radical that corresponds to the radical $R_1$ and has one fewer carbon atom, or represents hydrogen.

The invention relates especially to the processes illustrated in the Examples for the manufacture of the compounds according to the invention and to the formulation processes.

A compound obtainable according to the invention can be converted into a different compound according to the invention in a manner known per se.

If the aromatic ring A has a hydrogen atom as substituent, the hydrogen atom can be replaced by a halogen atom in customary manner using a halogenation agent, for example by bromination with bromine, hypobromic acid, acylhypobromites or other organic bromine compounds, for example N-bromosuccinimide, N-bromoacetamide, N-bromophthalimide, pyridinium perbromide, dioxane dibromide, 1,3-dibromo-5,5-dimethylhydantoin, 2,4,4,6-tetrabromo-2,5-cyclohexadien-1-one, or by chlorination, advantageously with elemental chlorine, for example in a halogenated hydrocarbon, such as chloroform, and while cooling, for example to from approximately $-10°$ to approximately $+10°$ C.

It is also possible to alkylate the benzo moiety of the ring system, for example with a lower alkanol or a lower alkyl halide or a phosphoric acid lower alkyl ester in the presence of Lewis acids (Friedel-Crafts alkylation). In a compound of the formula (I) in which the aromatic ring A contains bromine, it is possible, for example, to replace the bromine by lower alkyl by reaction with a lower alkyl bromine in the presence of an alkali metal.

If the aromatic ring A contains a hydrogen atom as substituent, then the hydrogen atom can be replaced by an acyl group in a manner known per se. Thus, for example, the introduction of the acyl group can be carried out analogously to the Friedel-Crafts acylation (cf. G. A. Olah, Friedel-Crafts and Related Reactions, Vol. I, Interscience, New York, 1963–1965), for example by reaction of a reactive functional acyl derivative, such as a halide or anhydride, of an organic carboxylic acid in the presence of a Lewis acid, such as aluminium, antimony-(III) or -(V), iron(III), tin(II) or zinc(II) chloride or boron trifluoride.

If the aromatic ring A contains hydroxy as substituent, then the hydroxy can be etherified in a manner known per se. The reaction with an alcohol component, for example with a lower alkanol, such as ethanol, in the presence of acids, for example a mineral acid, such as sulphuric acid, or in the presence of dehydrating agents, such as dicyclohexyl carbodiimide, results, for example, in lower alkoxy. Conversely, ethers can be cleaved to form phenols by cleaving the ethers using acids, such as mineral acids, for example hydrohalic acid, such as hydrobromic acid, or such as Lewis acids, for example halides of elements of main group III, such as boron tribromide, or using pyridine hydrochloride or thiophenol.

Furthermore, hydroxy can be converted into lower alkanoyloxy, for example by reaction with a desired lower alkanecarboxylic acid, such as acetic acid, or a reactive derivative thereof, for example in the presence of an acid, such as a protonic acid, for example hydrochloric or hydrobromic acid, sulphuric acid, phosphoric acid or a benzenesulphonic acid, in the presence of a Lewis acid, for example boron trifluoride etherate, or in the presence of a water-binding agent, such as dicyclohexyl carbodiimide. Conversely, esterified hydroxy can be solvolysed to form hydroxy, for example by base catalysis.

If the ring A is substituted by lower alkylthio, the lower alkylthio can be oxidised in customary manner to form the corresponding lower alkane-sulphinyl or -sulphonyl. There come into consideration as suitable oxidising agents for the oxidation to the sulphoxide stage, for example, inorganic peracids, such as peracids of mineral acids, for example periodic acid or persulphuric acid, organic peracids, such as corresponding percarboxylic or persulphonic acids, for example performic, peracetic, trifluoroperacetic, m-chloroperbenzoic or perbenzoic acid, or p-toluenepersulphonic acid, or mixtures of hydrogen peroxide and acids, for example a mixture of hydrogen peroxide and acetic acid.

The oxidation is often carried out in the presence of suitable catalysts; there may be mentioned as catalysts suitable acids, such as optionally substituted carboxylic acids, for example acetic acid or trifluoroacetic acid, or transition metal oxides, such as oxides of elements of sub-group VII, for example vanadium, molybdenum or tungsten oxide. The oxidation is carried out under mild conditions, for example at temperatures of from approximately $-50°$ to approximately $+100°$ C.

The oxidation to the sulphone stage can also be carried out in corresponding manner using dinitrogen tetroxide as catalyst in the presence of oxygen at low temperatures, as can the direct oxidation of the lower alkylthio to form lower alkanesulphonyl. In this case, however, the oxidising agent is customarily used in excess.

Hydrogen $R_1$ may be converted into alkyl $R_1$, for example by alkylation, for example with a reactive esterified alkohol of the formula $R_1$—OH, such as a corresponding halogenid or a sulfonyloxy derivative thereof, especially in the presence of a strong base. The alkylation may be take place, for example, by a previous substitution of hydrogen $R_1$ by halogen and subsequent reaction with metallic compounds of the formula $R_1$—Me, Me being, for example, an alkaline metal, earth alkaline metal halogenide or Li—Cu.

If the compounds of the formula (I) contain unsaturated radicals, such as lower alkenyl or lower alkenylene groupings, the unsaturated radicals may be converted into saturated radicals in a manner known per se. Thus, for example, the hydrogenation of multiple bonds is carried out by catalytic hydrogenation in the presence of hydrogenation catalysts; suitable catalysts for this purpose are, for example, noble metals or derivatives thereof, for example oxides, such as nickel, Raney nickel, palladium or platinum oxide, all of which may optionally be supported on carriers, for example on carbon or calcium carbonate. The hydrogenation can be carried out preferably at pressures of from 1 to approximately 100 atm. and at temperatures of from approximately $-80°$ to approximately $200°$ C., especially from room temperature to approximately $100°$ C. The reaction is advantageously carried out in a solvent, such as water, a lower alkanol, for example ethanol, isopropanol or n-butanol, an ether, for example dioxan, or a lower alkanecarboxylic acid, for example acetic acid.

Conversely, in cyclic systems $R_2$, one or more multiple bonds can be introduced. For this purpose, suitable dehydrogenation agents are used, for example elements of the sub-groups, preferably those of sub-group VII of the Periodic Table for example palladium or platinum, or corresponding derivatives of noble metals, for example ruthenium triphenylphosphide chloride, it being possible for the agents to be supported on suitable carriers. Further preferred dehydrogenation agents are, for example, quinones, such as p-benzoquinones, for example tetrachloro-p-benzoquinone or 2,3-dichloro-5,6-dicyano-p-benzoquinone, or such as anthraquinones or phenanthren-9,10-quinone. It is also possible to use N-halosuccinimides, such as N-chlorosuccinimide, manganese compounds, such as barium manganate or manganese dioxide, and selenium derivatives, such as selenium dioxide or diphenylselenium bis-trifluoroacetate.

Salts of compounds of the formula (I) can be manufactured in a manner known per se. Thus, for example, acid addition salts of compounds of the formula (I) are obtained by treatment with an acid or a suitable ion exchange reagent. Salts can be converted in a customary manner into the free compounds; acid addition salts can be converted, for example, by treatment with a suitable basic agent.

Depending on the method of manufacture and the reaction conditions, the compounds according to the invention having salt-forming, especially basic, properties, may be obtained in free form or in the form of salts.

As a result of the close relationship between the novel compounds in free form and in the form of their salts, hereinbefore and hereinafter the free compounds or their salts shall be understood to mean optionally also the corresponding salts or free compounds, respectively, where appropriate with regard to meaning and purpose.

The novel compounds, including the salts of salt-forming compounds, can also be obtained in the form of their hydrates or include other solvents used for crystallisation.

Depending upon the starting materials and methods chosen, the novel compounds may be in the form of one of the possible isomers or in the form of mixtures thereof, for example, depending on the number of asymmetric carbon atoms, in the form of pure optical isomers, such as antipodes, or in the form of mixtures of isomers, such as racemates, mixtures of diastereoisomers or mixtures of racemates.

Resulting mixtures of diastereoisomers and mixtures of racemates can be separated on the basis of the physico-chemical differences between the constituents, in known manner, into the pure isomers, diastereoisomers or racemates, for example by chromatography and/or fractional crystallisation. Resulting racemates can furthermore be resolved into the optical antipodes by known methods, for example by recrystallisation from an optically active solvent, with the aid of microorganisms or by converting into diastereoisomeric salts or esters, for example by reacting an acidic end product with an optically active base that forms salts with the racemic acid, or with an optically active carboxylic acid or a reactive derivative thereof, and separating the mixture of diastereoisomers obtained in this manner, for example on the basis of their different solubilities, into the diastereoisomers, from which the desired enantiomer can be freed by the action of suitable agents. Advantageously, the more active enantiomer is isolated.

The invention relates also to those embodiments of the process according to which compounds obtainable as intermediates at any stage of the process are used as starting materials and the remaining steps are carried out or a starting material is used in the form of a derivative or a salt and/or the racemates or antipodes thereof or, especially, is formed under the reaction conditions.

In the process of the present invention it is preferable to use those starting materials which result in the compounds described at the beginning as being especially valuable. The invention relates also to novel starting materials, which have especially been developped for the preparation of the compounds according to the invention, their use and to processes for their manufacture, $R_1$, $R_2$ And A each having the meanings of the preferred compounds of groups of compounds of the formula I as indicated.

The invention relates also to the use of compounds of the formula (I) or of pharmaceutically acceptable salts of those compounds having salt-forming properties especially as pharmacological active ingredients, especially having an anti-inflammatory, analgesic and/or anti-pyretic action. They can be used, preferably in the form of pharmaceutically acceptable preparations, in a method for the prophylactic and/or therapeutic treatment of the human or animal body, especially for the treatment of disorders of the rheumatic type.

The invention relates also to pharmaceutical preparations that contain the compounds according to the invention, or pharmaceutically acceptable salts thereof, as active ingredients, and also to processes for their manufacture.

The pharmaceutical preparations according to the invention, which contain the compound according to the invention or pharmaceutically acceptable salts thereof, are for enteral, such as oral or rectal, and parenteral administration, and also for topical application to (a) warm-blooded animal(s) and contain the pharmacological active ingredient alone or together with a pharmaceutically acceptable carrier. The daily dosage of the active ingredient depends on age and the individual condition, and on the method of administration.

The novel pharmaceutical preparations contain, for example, from approximately 10% to approximately 80%, preferably from approximately 20% to approximately 60%, of active ingredient. Pharmaceutical preparations according to the invention for enteral or parenteral administration are, for example, those in dosage unit forms, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes, using, for example, corn, wheat, rice or potato starch, gelatine, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-fill capsules consisting of gelatine and also soft, sealed capsules consisting of gelatine and a plasticiser, such as glycerine or sorbitol. The dry-fill capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

There come into consideration as pharmaceutical preparations for topical application especially creams, ointments, pastes, foams, tinctures and solutions that contain from approximately 0.1% to 5% of active ingredient and can also be manufactured in a manner known per se.

The dosage of the active ingredient depends on the species of warm-blooded animal, age and individual condition, and on the method of administration. In normal cases, the estimated approximate daily dose in the case of oral administration to a warm-blooded animal weighing approximately 75 kg is from approximately 100 to approximately 600 mg, advantageously divided into several equal partial doses.

The following Examples illustrate the invention described above but are not intended to limit the scope of the invention in any way. Temperatures are given in degrees Centigrade.

EXAMPLE 1

1.2 ml (8.0 mmole) of 1,8-diazabicyclo[5.4.0]-undec-7-ene (DBU) are added at 0° to a solution of 2.50 g (7.8 mmole) of 1-bromo-2-[5-chloro-2-hydroxy-4-(piperidin-1-yl)-phenyl]-ethane in 50 ml of absolute methylene chloride and the whole is then stirred for 3 hours at room temperature. The reaction mixture is washed with saturated sodium chloride solution and the organic phases are combined, dried over sodium sulphate and concentrated in a vacuum rotary evaporator. The residue is chromatographed over silica gel using methylene chloride as eluant. Recrystallisation from petroleum ether yields 5-chloro-6-(piperidin-1-yl)-2,3-dihydrobenzofuran having a melting point of 38°–40°.

The starting material can be manufactured as follows:

177 g (1.0 mole) of 3,4-dichloroanisole [H. Jamarlik et al., Comptes Rendus Acad. Sci. Ser. C 273 (25), 1756 (1971)] are added carefully to a suspension, cooled to 0°, of 173.3 g (1.3 mole) of aluminium trichloride in 600 ml of absolute methylene chloride. 85 ml (1.2 mole) of acetyl chloride are then added dropwise thereto and the whole is stirred for 90 minutes at 0°. The reaction mixture is poured onto ice and extracted with methylene chloride. The organic extracts are washed with water, combined, dried over sodium sulphate and concentrated by evaporation in a vacuum rotary evaporator. Recrystallisation from ether/petroleum ether or methanol/water yields 4,5-dichloro-2-methoxyacetophenone having a melting point of 93°–95°.

A solution of 76.7 g (0.35 mole) of 4,5-dichloro-2-methoxyacetophenone in 750 ml of piperidine is maintained at 170° in an autoclave for 7 hours. The reaction mixture is concentrated by evaporation, taken up in ethyl acetate and washed with water. The ethyl acetate extracts are combined, dried over sodium sulphate and concentrated by evaporation in a vacuum rotary evaporator. The residue is chromatographed over silica gel with methylene chloride. In that manner, 5-chloro-2-hydroxy-4-(piperidin-1-yl)-acetophenone is obtained having a melting point of 68°–70°.

A solution of 32.5 g (128 mmole) of 5-chloro-2-hydroxy-4-(piperidin-1-yl)-acetophenone together with 75 ml (166 mmole) of an approximately 40% methanolic solution of benzyltriethylammonium hydroxide (Triton B) in 65 ml of tetrahydrofuran is cooled to 0°. 14.6 ml (154 mmole) of dimethyl sulphate are added dropwise over a period of approximately 6 minutes in such a manner that the internal temperature does not exceed 5°. The reaction mixture is stirred for a further 1 hour at 0°, then boiled under reflux for approximately 30 minutes. The reaction mixture is then poured into 400 ml of water and extracted with ethyl acetate. The combined ethyl acetate phases are washed with water, dried over sodium sulphate and concentrated by evaporation in a vacuum rotary evaporator. The residue is recrystallised from methylene chloride/hexane and 5-chloro-2-methoxy-4-(piperidin-1-yl)-acetophenone is obtained having a melting point of 119°–120°.

A solution of 18.2 g (68 mmole) of 5-chloro-2-methoxy-4-(piperidin-1-yl)-acetophenone and 4.36 g (136 mmole) of sulphur in 68 ml of morpholine is maintained at 90° for 5 hours. The reaction mixture is cooled, diluted with ethyl acetate and washed with water. The combined ethyl acetate extracts are dried over sodium sulphate and concentrated by evaporation in a vacuum rotary evaporator. Recrystallisation from methylene chloride/methanol yields 5-chloro-2-methoxy-4-(piperidin-1-yl)-phenylthioacetic acid morpholinamide having a melting point of 137°–139°.

A solution of 11.07 g (30 mmole) of 5-chloro-2-methoxy-4-(piperidin-1-yl)-phenylthioacetic acid morpholinamide in 120 ml of glacial acetic acid and 30 ml of concentrated hydrochloric acid is boiled under reflux for 22 hours. The reaction mixture is cooled, diluted with water and extracted with methylene chloride. The combined methylene chloride phases are washed with water, dried over sodium sulphate and concentrated by evaporation in a vacuum rotary evaporator. Chromatography over silica gel with chloroform/methanol (19:1) yields 5-chloro-2-methoxy-4-(piperidin-1-yl)-phenylacetic acid which after recrystallisation with methylene chloride/hexane melts at 120°–122°.

A solution of 14.2 g (50 mmole) of 5-chloro-2-methoxy-4-(piperidin-1-yl)-phenylacetic acid in 50 ml of absolute tetrahydrofuran is added dropwise over a period of approximately 15 minutes to a suspension of 1.6 g (42 mmole) of lithium aluminium hydride in 90 ml of absolute tetrahydrofuran. The whole is subsequently stirred for a further 2 hours at 50°. After the addition of 50 ml of water, the whole is filtered over Hyflo and then washed with THF. The solvent is concentrated in a vacuum rotary evaporator and the residue is partitioned between ether and water. The ether phases are combined, dried over sodium sulphate and concentrated in a vacuum rotary evaporator. The residue is chromatographed over silica gel using chloroform/ethyl acetate (1:1) as eluant. Recrystallisation from ether/petroleum ether yields 2-[5-chloro-2-methoxy-4-(piperidin-1-yl)-phenyl]-ethanol having a melting point of 56°–57°.

5.0 ml of boron tribromide are added dropwise over a period of approximately 5 minutes to a solution, cooled to 0°, of 2.70 g (10 mmole) of 2-[5-chloro-2-methoxy-4-(piperidin-1-yl)-phenyl]-ethanol in 70 ml of absolute methylene chloride. The reaction mixture is then stirred for a further 5 hours at room temperature, poured onto ice and the resulting suspension is adjusted to pH 6–7 with solid sodium carbonate and extracted with methylene chloride. The organic extracts are washed with water, combined, dried over sodium sulphate and concentrated in a vacuum rotary evaporator. Recrystallisation from petroleum ether yields 1-bromo-2-[5-chloro-2-hydroxy-4-(piperidin-1-yl)-phenyl]-ethane, melting point 115°–116°.

EXAMPLE 2

A solution of 1.4 g (5.2 mmole) of 5-chloro-3-hydroxy-3-methyl-6-(piperidin-1-yl)-2,3-dihydrobenzofuran in 20 ml of acetic acid/5N hydrochloric acid 1:1 is maintained at 85° for one hour. The reaction mixture is concentrated in a vacuum rotary evaporator, water is added to the residue and the whole is adjusted to pH 7 with saturated sodium carbonate solution and extracted with methylene chloride. The organic phases are washed with water, combined, dried over sodium sulphate and concentrated in a vacuum rotary evaporator. Chromatography over silica gel using chloroform as eluant yields 5-chloro-3-methyl-6-(piperidin-1-yl)-benzofuran which, after recrystallisation from petroleum ether, melts at 82°–84°.

The starting material can be manufactured as follows:

6.0 ml (0.12 mole) of bromine are added dropwise over a period of approximately 5 minutes to a solution of 25.2 g (0.10 mole) of 5-chloro-2-hydroxy-4-(piperidin-1-yl)-acetophenone in 240 ml of chloroform. The reaction mixture is stirred for 4 hours at room temperature, water is added and the whole is adjusted to pH 6–7 with dilute sodium bicarbonate solution. The organic phase is separated, washed with water, dried over sodium sulphate and concentrated in a vacuum rotary evaporator. The residue is chromatographed over silica gel using toluene as eluant. Recrystallisation from isopropanol/petroleum ether yields 5-chloro-2-hydroxy-4-(piperidin-1-yl)-bromoacetophenone having a melting point of 92°–94°.

10.0 g (120 mmole) of sodium acetate are added to a solution, cooled to −10°, of 10.0 g (30 mmole) of 5- chloro-2-hydroxy-4-(piperidin-1-yl)-bromoacetophenone in 80 ml of dimethylformamide and the whole is stirred for one hour at 0°. The reaction mixture is subsequently diluted with water and extracted three times with ethyl acetate. The organic phases are washed with water, combined, dried over sodium sulphate and concentrated in a vacuum rotary evaporator. In that manner, 5-chloro-6-(piperidin-1-yl)-benzofuran-3(2H)-one is obtained in the form of an oil having an $R_f$ of 0.3 (silica gel/methylene chloride) which is used in the following reactions without further purification.

A solution of 5.03 g (20.0 mmole) of crude 5-chloro-6-(piperidin-1-yl)-benzofuran-3(2H)-one in 30 ml of absolute ether is added dropwise at room temperature to a freshly prepared Grignard solution of 750 mg (30.8 mmole) of magnesium filings and 4.0 g (28.2 mmole) of methyl iodide in 30 ml of absolute ether. The whole is subsequently boiled under reflux for 45 minutes and poured onto ice/ammonium chloride. The ether phase is separated off and the aqueous phase is extracted twice more with ether. The organic phases are washed with water, combined, dried over sodium sulphate and concentrated in a vacuum rotary evaporator. Chromatography over silica gel with chloroform/ethyl acetate (10:1) yields 5-chloro-3-hydroxy-3-methyl-6-(piperidin-1-yl)-2,3-dihydrobenzofuran in the form of an oil having an $R_f$ of 0.24 [silica gel, chloroform/ethyl acetate (10:1)].

EXAMPLE 3

A solution of 2.40 g (9.4 mmole) of 5-chloro-3-hydroxy-6-(piperidin-1-yl)-2,3-dihydrobenzofuran in 25 g of polyphosphoric acid is maintained at 60° for 20 minutes, then ice and water are added and the whole is adjusted to pH 7 with solid sodium carbonate. The reaction mixture is extracted twice with methylene chloride. The organic phases are washed with water, combined, dried over magnesium sulphate and concentrated in a vacuum rotary evaporator. The residue is chromatographed over silica gel using methylene chloride as eluant ($R_f$=0.63). In that manner, 5-chloro-6-(piperidin-1-yl)-benzofuran is obtained in the form of an oil which distills at 96°–97°/1.5 torr.

The starting material can be manufactured as follows:

528 mg (13.1 mmole) of sodium borohydride are added to a solution, cooled to 0°, of 3.3 g (13.1 mmole) of 5-chloro-6-(piperidin-1-yl)-benzofuran-3(2H)-one, according to Example 2, in 80 ml of methanol. The whole is subsequently stirred for a further 4 hours at 0°. The reaction mixture is diluted with water, adjusted to pH 6–7 with dilute ammonium chloride solution and extracted several times with methylene chloride. The organic phases are washed with water, combined, dried over sodium sulphate and concentrated in a vacuum rotary evaporator. Chromatography over silica gel using methylene chloride as eluant ($R_f$=0.12) yields 5-chloro-3-hydroxy-6-(piperidin-1-yl)-2,3-dihydrobenzofuran in the form of an oil.

EXAMPLE 4

200 mg of platinum oxide are added to a solution of 1.38 g (5.5 mmole) of 5-chloro-6-(piperidin-1-yl)-benzofuran-3(2H)-one in 20 ml of ethanol and the whole is hydrogenated at 3 atmospheres. The catalyst is filtered off and the filtrate is concentrated in a vacuum rotary evaporator. The residue is chromatographed over silica gel using methylene chloride as eluant. Recrystallisation from petroleum ether yields 5-chloro-6-(piperidin-1-yl)-2,3-dihydrobenzofuran having a melting point of 38°–40°.

EXAMPLE 5

A solution of 2.37 g (10.0 mmole) of 5-chloro-6-(piperidin-1-yl)-2,3-dihydrobenzofuran and 2.27 g (10.0 mmole) of 2,3-dichloro-5,6-dicyano-1,4-benzoquinone in 200 ml of dioxane is boiled under reflux for 12 hours. The reaction mixture is cooled and filtered and the filtrate is concentrated in a vacuum rotary evaporator. The residue is chromatographed over silica gel using methylene chloride as eluant ($R_f$=0.63). In that manner, 5-chloro-6-(piperidin-1-yl)-benzofuran is obtained in the form of an oil which distills at 96°–97°/1.5 torr.

EXAMPLE 6

200 mg of platinum oxide are added to a solution of 1.42 g (5.60 mmole) of 5-chloro-3-hydroxy-6-(piperidin-1-yl)-2,3-dihydrobenzofuran in 20 ml of ethanol and the whole is hydrogenated at 3 atmospheres. The catalyst is filtered off and the filtrate is concentrated in a vacuum rotary evaporator. The residue is chromatographed over silica gel using methylene chloride as eluant. Recrystallisation from petroleum ether yields 5-chloro-6-(piperidin-1-yl)-2,3-dihydrobenzofuran having a melting point of 38°–40°.

EXAMPLE 7

A solution of 25.3 g (0.10 mole) of 5-chloro-2-hydroxy-4-(piperidin-1-yl)-acetophenone, 18.4 g (0.11 mole) of bromoacetic acid ethyl ester and 13.8 g (0.10 mole) of potassium carbonate in 500 ml of absolute acetone is boiled under reflux for 12 hours. The reaction mixture is cooled and filtered and the acetone is concentrated in a vacuum rotary evaporator. The residue is taken up in water and extracted with methylene chloride. The organic phases are washed with water, combined, dried over sodium sulphate and concentrated in a vacuum rotary evaporator. Rapid filtration over silica gel using methylene chloride/petroleum ether (5:1) as eluant yields 2-[2-acetyl-4-chloro-5-(piperidin-1-yl)-phenoxy]-ethyl acetate to which, without further purification, 100 ml of 2N sodium hydroxide solution and 100 ml of ethanol are added and the whole is boiled under reflux for 15 minutes. The mixture is adjusted to pH 5–6 with dilute hydrochloric acid and extracted with methylene chloride. The organic phases are washed with water, combined, dried over sodium sulphate and concentrated in a vacuum rotary evaporator. The residue is taken up in 100 ml of acetic anhydride, 16 g (0.20 mole) of sodium acetate are added and the whole is boiled under reflux for 2 hours. The reaction mixture is cooled, diluted with water, adjusted to pH 6–7 with dilute sodium carbonate solution and extracted with methylene chloride. The organic phases are washed with water, combined, dried over sodium sulphate and concentrated in a vacuum rotary evaporator. Chromatography over silica gel using chloroform as eluant yields 5-chloro-3-methyl-6-(piperidin-1-yl)-benzofuran which, after recrystallisation from petroleum ether, melts at 82°–84°.

EXAMPLE 8

A solution of 2.51 g (10.0 mmole) of 5-chloro-6-(piperidin-1-yl)-benzofuran-3(2H)-one in 15 ml of acetic anhydride and 15 ml of glacial acetic acid is maintained at 100° for 24 hours. The reaction mixture is subsequently poured onto ice and extracted with methylene chloride. The organic phases are washed with water, combined, dried over sodium sulphate and concentrated in a vacuum rotary evaporator. The crude 3-acetoxy-5-chloro-6-(piperidin-1-yl)-benzofuran so obtained is dissolved in 15 ml of absolute methanol, 250 mg of platinum oxide are added and the whole is hydrogenated at 3 atmospheres and room temperature. The catalyst is filtered off and the filtrate is concentrated in a vacuum rotary evaporator. The residue is chromatographed over silica gel using methylene chloride as eluant ($R_f$=0.63). In that manner, 5-chloro-6-(piperidin-1-yl)-benzofuran is obtained in the form of an oil which distills at 96°–97°/1.5 torr.

EXAMPLE 9

A solution of 250 mg (1.00 mmole) of crude 5-chloro-2-hydroxy-6-(piperidin-1-yl)-2,3-dihydrobenzofuran in 2.5 g of polyphosphoric acid is maintained at 60° for 20 minutes, then ice and water are added and the whole is adjusted to pH 7 with solid sodium carbonate. The reaction mixture is extracted twice with methylene chloride. The organic phases are washed with water, combined, dried over sodium sulphate and concentrated in a vacuum rotary evaporator. The residue is chromatographed over silica gel using methylene chloride as eluant ($R_f$=0.63). In that manner, 5-chloro-6-(piperidin-1-yl)-benzofuran is obtained in the form of an oil which distills at 96°–97°/1.5 torr.

The starting material can be manufactured as follows:

A solution of 8.5 g (30 mmole) of 5-chloro-2-methoxy-4-(piperidin-1-yl)-phenylacetic acid in 150 ml of 48% hydrobromic acid is boiled under reflux for 15 hours. The reaction mixture is cooled, diluted with water and adjusted to pH 3–4 with saturated sodium bicarbonate solution. The whole is subsequently extracted with ethyl acetate and the combined organic phases are washed with water, dried over sodium sulphate and concentrated by evaporation in a vacuum rotary evaporator. In that manner a dark grey foam of 5-chloro-2-hydroxy-4-(piperidin-1-yl)-phenylacetic acid is obtained which is reacted, without purification, to form 5-chloro-6-(piperidin-1-yl)-benzofuran-2(3H)-one.

A solution of 6.5 g (31.5 mmole) of dicyclohexyl carbodiimide in 40 ml of absolute methylene chloride is added at room temperature over a period of approximately 3 minutes to a solution of 8.1 g (30 mmole) of crude 5-chloro-2-hydroxy-4-(piperidin-1-yl)-phenylacetic acid in 50 ml of absolute methylene chloride. The reaction mixture is stirred for 30 minutes at room temperature. The precipitated dicyclohexylurea is filtered with suction and washed with methylene chloride. The filtrate is concentrated by evaporation in a vacuum rotary evaporator and the residue is chromatographed over silica gel using methylene chloride/hexane (1:1) as eluant. recrystallisation from hexane yields 5-chloro-6-(piperidin-1-yl)-benzofuran-2(3H)-one having a melting point of 129°–131°.

A solution of 251 mg (1.00 mmole) of 5-chloro-6-(piperidin-1-yl)-benzofuran-2(3H)-one in 5 ml of absolute tetrahydrofuran is cooled to −78° under a nitrogen atmosphere, 0.84 ml (1.00 mmole) of a 20% diisobutyl aluminium hydride solution in toluene is added and the whole is stirred for 30 minutes at −78°. 2 ml of 2N sulphuric acid are then added and the whole is stirred for 15 minutes at −40°. The reaction mixture is diluted with water and extracted with methylene chloride. The organic phases are washed with water, combined, dried over sodium sulphate and concentrated in a vacuum rotary evaporator. 5-chloro-2-hydroxy-6-(piperidin-1-yl)-2,3-dihydrobenzofuran is obtained in the form of an oil which is used for the following reactions without purification. $R_f$ [silica gel, chloroform/ethyl acetate (3:1)]=0.48.

EXAMPLE 10

5 mg of platinum oxide are added to a solution of 250 mg (1.00 mmole) of crude 5-chloro-2-hydroxy-6-(piperidin-1-yl)-2,3-dihydrobenzofuran in 5 ml of absolute ethanol and the whole is hydrogenated at room temperature and 3 atmospheres. The catalyst is filtered off and the filtrate is concentrated in a vacuum rotary evaporator. The residue is chromatographed over silica gel using methylene chloride as eluant. Recrystallisation from petroleum ether yields 5-chloro-6-(piperidin-1-yl)-2,3-dihydrobenzofuran having a melting point of 38°–40°.

EXAMPLE 11

A mixture of 9.98 g (50 mmole) of 1-(3-amino-4-chlorophenoxy)-2-propanone, 22.9 g (0.10 mole) of 1,5-dibromopentane, 12.9 g (0.10 mole) of N-ethyldiisopropylamine and 60 ml of ethanol is boiled under reflux for 18 hours. The residue obtained after concentration by evaporation in vacuo is taken up in methylene chloride and washed twice with dilute sodium bicarbonate solution. The organic phase is dried, concentrated by evaporation and the crude product is taken up in 250 ml of ethanol, 40 ml of concentrated hydrochloric acid are added and the whole is boiled under reflux for 30 hours. The ethanol is concentrated in a vacuum rotary evaporator and the residue is diluted with ice-water, rendered alkaline with 6N sodium hydroxide solution and extracted with methylene chloride. The organic phases are washed with water, combined, dried over sodium sulphate and concentrated in a vacuum rotary evaporator. Chromatography over silica gel using chloroform as eluant yields 5-chloro-3-methyl-6-(piperidin-1-yl)-benzofuran which, after recrystallisation from petroleum ether, melts at 82°–84°.

EXAMPLE 12

A mixture of 9.1 g (50 mmole) of 6-amino-5-chloro-3-methylbenzofuran, 11.8 ml (0.1 mole) of 1,4-dibromobutane, 17.1 ml (0.1 mole) of N-ethyldiisopropylamine and 60 ml of ethanol is boiled under reflux for 24 hours and then concentrated by evaporation in vacuo. The residue is partitioned between methylene chloride and saturated sodium bicarbonate solution. The crude product obtained after drying and concentration by evaporation of the methylene chloride is chromatographed with petroleum ether/ether over silica gel. Subsequent distillation in a bulb tube (150°/10$^{-1}$ torr) yields 5-chloro-3-methyl-6-(pyrrolidin-1-yl)-benzofuran having a melting point of 50°–52°.

The starting material can be manufactured as follows:

A mixture of 14.2 g (82 mmole) of 4-chloro-3-nitrophenol, 12.4 g (90 mmole) of ground potassium carbonate, 8.2 g (55 mmole) of sodium iodide, 8.3 g (90 mmole) of chloroacetone and 220 ml of dimethylformamide is stirred for 3 hours at room temperature. The whole is subsequently filtered, the residue is washed with dimethylformamide, the organic phase is concentrated by evaporation in vacuo and the resulting crude product is partitioned between water and methylene chloride. The solid remaining after drying and removal of the methylene chloride is recrystallised from methylene chloride/petroleum ether. 1-(4-chloro-3-nitrophenoxy)-2-propanone is obtained having a melting point of 92°–94°.

A mixture of 23.8 g (0.104 mole) of 1-(4-chloro-3-nitrophenoxy)-2-propanone, 2 g of Raney nickel and 240 ml of dioxane is hydrogenated at normal pressure and room temperature. After 20 hours (hydrogen absorption: 103%), the whole is filtered with suction over Celite, then washed with dioxane and concentrated by evaporation in vacuo. Purification of the crude product by chromatographed with petroleum ether/ether over silica gel and subsequent recrystallisation from ether/petroleum ether yields 1-(3-amino-4-chlorophenoxy)-2-propanone having a melting point of 49°–51°.

A mixture of 11.4 g (57 mmole) of 1-(3-amino-4-chlorophenoxy)-2-propanone, 10 ml of concentrated hydrochloric acid and 150 ml of ethanol is boiled under reflux for 14 hours and subsequently concentrated by evaporation in vacuo. Ice-water is added to the residue and the whole is rendered alkaline with 3N sodium hydroxide solution and extracted with ether. The crude product obtained after drying and concentration by evaporation of the organic phase is chromatographed over silica gel with petroleum ether/methylene chloride. Recrystallisation of the pure fractions from ether/petroleum ether yields 6-amino-5-chloro-3-methylbenzofuran having a melting point of 73°–75°.

EXAMPLE 13

5 ml of 6N hydrochloric acid are added to a mixture of 7.5 g (46.5 mmole) of 6-amino-3,5-dimethylbenzofuran, 7.5 ml (58 mmole) of 2,5-dimethoxytetrahyrofuran and 150 ml of dioxane and the whole is boiled under reflux for 40 minutes. The whole is concentrated by evaporation in vacuo and the residue is taken up in methylene chloride and washed three times with water. The crude product obtained after drying and concentration by evaporation of the organic phase is chromatographed over silica gel with petroleum ether/ether. Subsequent distillation of the pure fractions in a bulb tube (120°/4.10$^{-2}$ torr) yields 3,5-dimethyl-6-(pyrrol-1-yl)-benzofuran having a melting point of 43°–45°.

The starting material can be manufactured as follows:

40.7 g (0.44 mole) of chloroacetone are added dropwise at room temperature, with stirring, over a period of 30 minutes to a suspension of 61.25 g (0.4 mole) of 4-methyl-3-nitrophenol, 60.8 g (0.44 mole) of ground potassium carbonate, 39.9 g (0.267 mole) of sodium iodide and 900 ml of dimethylformamide. After a further 3 hours at room temperature, the whole is filtered with suction and the residue is washed with dimethylformamide. The organic solution is concentrated by evaporation in vacuo and the resulting crude product is partitioned between methylene chloride and water. The residue remaining after drying and removal of the methylene chloride is chromatographed over silica gel with petroleum ether/methylene chloride. Subsequent recrystalliation from methylene chloride/petroleum ether yields 1-(4-methyl-3-nitrophenoxy)-2-propanone having a melting point of 84°–86°.

A mixture of 96.2 g (0.46 mole) of 1-(4-methyl-3-nitrophenoxy)-2-propanone, 10 g of 5% palladium on carbon and 960 ml of dioxane is hydrogenated for 6 hours at room temperature. The catalyst is subsequently filtered off and the filtrate is concentrated by evaporation in vacuo. The resulting residue is taken up in 2.5 liters of ethanol, 400 ml of concentrated hydrochloric acid are added and the whole is boiled under reflux for 30 hours. The ethanol is removed in vacuo and the residue is diluted with ice-water, rendered alkaline with 6N sodium hydroxide solution and extracted with ether. The crude product obtained after drying and concentration by evaporation of the organic phase is chromatographed over silica gel with methylene chloride/acetone. Recrystallisation of the pure fractions from petroleum ether yields 6-amino-3,5-dimethylbenzofuran having a melting point of 64°–65°.

EXAMPLE 14

A mixture of 22.8 g (0.141 mole) of 6-amino-3,5-dimethylbenzofuran, 65.8 g (0.283 mole) of 2,2'-dibromodiethyl ether, 36.1 g (0.279 mole) of N-ethyldiisopropylamine and 210 ml of ethanol is boiled under reflux for 16 hours. The residue obtained after removal of the ethanol in vacuo is taken up in methylene chloride and washed twice with dilute sodium bicarbonate solution. The organic phase is dried, concentrated by evaporation and the crude product is chromatographed over silica gel with petroleum ether/ether. The excess 2,2'-dibromodiethyl ether is removed in a water-jet vacuum over a Vigreux column and the residue is purified by means of solid distillation (110°–115°/4.10$^{-2}$ torr). 3,5-dimethyl-6-morpholinobenzofuran is obtained having a melting point of 69°–70°.

EXAMPLE 15

A mixture of 8 g (49.6 mmole) of 6-amino-3,5-dimethylbenzofuran, 23 g (0.1 mole) of 1,5-dibromopentane, 12.9 g (0.1 mole) of N-ethyldiisopropylamine and 60 ml of ethanol is boiled under reflux for 18 hours. The residue obtained after concentration by evaporation in vacuo is taken up in methylene chloride and washed twice with dilute sodium bicarbonate solution. The organic phase is dried, concentrated by evaporation and the crude product is chromatographed with petroleum ether/methylene chloride over silica gel. Distillation of the pure fractions in a bulb tube (130°/10$^{-1}$ torr) yields 3,5-dimethyl-6-piperidinobenzofuran having a melting point of 64°–66°.

EXAMPLE 16

7 ml of 5N hydrochloric acid are added to a mixture of 9.1 g (50 mmole) of 6-amino-5-chloro-3-methylbenzofuran, 10 ml (78 mmole) of 2,5-dimethoxytetrahydrofuran and 200 ml of dioxane and the whole is stirred at room temperature for 16 hours. The whole is subsequently concentrated by evaporation in vacuo and the residue is chromatographed over silica gel with petroleum ether/methylene chloride. Crystallisation of the resulting product from petroleum ether yields 5-chloro-3-methyl-6-(pyrrol-1-yl)-benzofuran having a melting point of 49°–52°.

EXAMPLE 17

A mixture of 10 g (43.2 mmole) of 3,5-dimethyl-6-morpholinobenzofuran, 2 g of 5% palladium on carbon and 200 ml of ethyl acetate is hydrogenated at room temperature and a pressure of 4 bar. For completion of the reaction, 2 g, each time, of 5% palladium on carbon are added a further four times during hydrogenation. After a total of 58 hours, the catalyst is filtered off and the filtrate is concentrated by evaporation in vacuo. Purification of the residue by flash chromatography (silica gel, petroleum ether/ether) and distillation of the pure fractions in a bulb tube (130°–140°/6.10$^{-2}$ torr)

yields 3,5-dimethyl-6-morpholino-2,3-dihydrobenzofuran having a melting point of 57°–58°.

EXAMPLE 18

A mixture of 8 g (37.9 mmole) of 3,5-dimethyl-6-(pyrrol-1-yl)-benzofuran, 1.6 g of 5% palladium on carbon and 80 ml of dioxane is hydrogenated at 35° and a pressure of 4 bar. To complete the reaction, 0.8 g, each time, of 5% palladium on carbon is added a further three times during hydrogenation. After a total of 100 hours, the catalyst is filtered off and the filtrate is concentrated by evaporation in vacuo. Chromatography of the residue over silica gel (petroleum ether/methylene chloride) and distillation of the pure fractions in a bulb tube (120°/2.10$^{-2}$ torr) yields 3,5-dimethyl-6-(pyrrol-1-yl)-2,3-dihydrobenzofuran in the form of a colourless oil.

$^1$H-NMR spectrum (250 MHz, CDCl$_3$, δ in ppm): 1.36 (d, J≈7 Hz, 3H); 2.11 (s, 3H); 3.57 (m, 1H); 4.12 (t, J≈8 Hz, 1H); 4.72 (t, J≈8 Hz, 1H); 6.29 (m, 2H); 6.69 (s, 1H); 6.75 (m, 2H); 7.04 (s, 1H).

EXAMPLE 19

2 ml of 6N hydrochloric acid are added to a mixture of 2.95 g (20 mmole) of 6-amino-5-methylbenzofuran, 3.17 g (24 mmole) of 2,5-dimethoxytetrahydrofuran and 50 ml of dioxane and the whole is boiled under reflux for 40 minutes. The whole is then concentrated in vacuo, the residue is taken up in methylene chloride and the organic phase is washed three times with water. The crude product remaining after drying and removal of the methylene chloride is chromatographed over silica gel with ether/petroleum ether. Subsequent distillation of the pure fractions in a bulb tube (105°, 5.10$^{-2}$ torr) yields 5-methyl-6-(pyrrol-1-yl)-benzofuran in the form of a pale yellow oil.

$^1$H-NMR spectrum (250 MHz, CDCl$_3$, δ in ppm): 2.23 (s, 3H); 6.32 (m, 2H); 6.74 (m, 1H); 6.80 (m, 2H); 7.42 (s, 1H); 7.48 (s, 1H); 7.65 (d, J≈2 Hz, 1H).

The starting material can be manufactured as follows:

A mixture of 15.3 g (0.1 mole) of 4-methyl-3-nitrophenol, 16.8 g (0.11 mole) of chloroacetaldehyde diethyl acetal, 20.7 g (0.15 mole) of ground potassium carbonate, 4.5 g (30 mmole) of sodium iodide and 100 ml of dimethylformamide is boiled under reflux for 12 hours. The whole is subsequently filtered with suction, the residue is washed with dimethylformamide and the solution is concentrated by evaporation in vacuo. Chromatography of the residue over silica gel (methylene chloride) and subsequent distillation of the pure fractions (105°–110°/6.10$^{-2}$ torr) yields 2-(4-methyl-3-nitrophenoxy)-acetaldehyde diethyl acetal in the form of a yellowish oil.

12.4 g (46.1 mmole) of this oil are taken up in 130 ml of tetrahydrofuran, 4 g of Raney nickel are added and the whole is hydrogenated at room temperature for 7.5 hours. The catalyst is subsequently filtered off and the filtrate is concentrated by evaporation. Distillation of the residue in a bulb tube (130°/5.10$^{-2}$ torr) yields 2-(3-amino-4-methylphenoxy)-acetaldehyde diethyl acetal in the form of a pale yellow oil.

2.39 g (10 mmole) of this oil are taken up in 75 ml of ethanol, 12 ml of concentrated hydrochloric acid are added and the whole is boiled under reflux for 3.5 hours. The ethanol is subsequently removed in vacuo and the residue is diluted with ice-water, rendered alkaline with 2N sodium hydroxide solution and extracted with ether. The crude product remaining after drying and concentration by evaporation of the organic phase is distilled in a bulb tube (130°/6.10$^{-2}$ torr). The distillate is chromatographed over silica gel with methylene chloride. Distillation of the pure column fractions in a bulb tube (120°/6.10$^{-2}$ torr) yields 6-amino-5-methyl-benzofuran having a melting point of 74°–76°.

EXAMPLE 20

5-methyl-6-(pyrrol-1-yl)-2,3-dihydrobenzofuran is obtained analogously to the methods described in Examples 1–19.

FORMULATION EXAMPLE 1

Tablets containing 25 mg of active ingredient, for example 3,5-dimethyl-6-(pyrrol-1-yl)-benzofuran, can be manufactured as follows:

Constituents (for 1000 tablets):
active ingredient 25.0 g
lactose 100.7 g
wheat starch 7.5 g
polyethylene glycol 6000 5.0 g
talc 5.0 g
magnesium stearate 1.8 g
demineralised water q.s.

Manufacture

All the solid ingredients are first passed through a sieve having a mesh width of 0.6 mm. The active ingredient, the lactose, the talc, the magnesium stearate and half of the starch are then mixed together. The other half of the starch is suspended in 40 ml of water and this suspension is added to a boiling solution of the polyethylene glycol in 100 ml of water. The resulting starch paste is added to the main mixture and the whole is granulated, if necessary with the addition of water. The granulate is dried overnight at 35°, passed through a sieve having a mesh width of 1.2 mm and pressed to form tablets approximately 6 mm in diameter that are concave on both sides.

FORMULATION EXAMPLE 2

Tablets for chewing containing 30 mg of active ingredient, for example 3,5-dimethyl-6-(pyrrol-1-yl)-benzofuran, can be manufactured as follows:

Composition (for 1000 tablets):
active ingredient 30.0 g
mannitol 267.0 g
lactose 179.5 g
talc 20.0 g
glycine 12.5 g
stearic acid 10.0 g
saccharine 1.0 g
5% gelatine solution q.s.

Manufacture

All of the solid ingredients are first passed through a sieve having a mesh width of 0.25 mm. The mannitol and lactose are mixed, granulated with the addition of gelatine solution, passed through a sieve having a mesh width of 2 mm, dried at 50° and passed through a sieve having a mesh width of 1.7 mm. The active ingredient, the glycine, and the saccharine are carefully mixed, the mannitol, the lactose granulate, the stearic acid and the talc are added and the whole is mixed thoroughly and pressed to form tablets approximately 10 mm in diameter that are concave on both sides and have a breaking groove on the upper side.

FORMULATION EXAMPLE 3

Tablets containing 100 mg of active ingredient, for example 3,5-dimethyl-6-(pyrrol-1-yl)-benzofuran, can be manufactured as follows:

Composition (for 1000 tablets):
active ingredient 100.0 g
lactose 248.5 g
corn starch 17.5 g
polyethylene glycol 6000 5.0 g
talc 15.0 g
magnesium stearate 4.0 g
demineralised water q.s.

Manufacture

The solid ingredients are first passed through a sieve having a mesh width of 0.6 mm. The active ingredient, the lactose, the talc, the magnesium stearate and half of the starch are then intimately mixed. The other half of the starch is suspended in 65 ml of water and this suspension is added to a boiling solution of the polyethylene glycol in 260 ml of water. The resulting paste is added to the pulverulent substances and the whole is mixed and granulated, if necessary with the addition of water. The granulate is dried overnight at 35°, passed through a sieve having a mesh width of 1.2 mm and pressed to form tablets approximately 10 mm in diameter that are concave on both sides and have a breaking notch on the upper side.

We claim:

1. Benzofurans or 2,3-dihydrobenzofurans of the formula

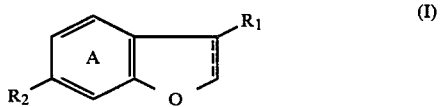

in which
$R_1$ represents hydrogen or an aliphatic radical,
$R_2$ represents an amino group disubstituted by a bivalent aliphatic radical which is optionally interrupted by at least one hetero atom,
and the aromatic ring
A may be additionally substituted,
and the salts thereof.

2. Compounds of the formula I according to patent claim 1 in which $R_1$ represents hydrogen, lower alkyl, lower alkenyl or lower alkynyl, $R_2$ represents lower alkyleneamino which may additionally have one or two ortho-fused benzo system(s), lower alkenyleneamino having one or two double bonds, wherein lower alkenyleneamino having one double bond may additionally have one ortho-fused benzo system, or lower alkyleneamino or lower alkenyleneamino having one double bond, each of which is interrupted in the lower alkylene or lower alkenylene moiety by at least one aza, lower alkylaza, oxa or thia group, and the aromatic ring A is additionally mono- or poly-substituted by lower alkyl, hydroxy-lower alkyl, halo-lower alkyl, lower alkenyl, alkylene bridging two adjacent carbon atoms and having 3 or 4 chain members, lower alkoxy, lower alkylthio, lower alkanesulphinyl, lower alkanesulphonyl, hydroxy, halogen, lower alkanoyloxy, lower alkanoyl and/or by nitro or, except for $R_2$, is unsubstituted, and the salts thereof.

3. Compounds of the formula I according to patent claim 1 in which $R_1$ represents hydrogen or lower alkyl, $R_2$ represents lower alkyleneamino which may additionally have one or two ortho-fused benzo system(s), lower alkenyleneamino having one or two double bonds, wherein lower alkenyleneamino having one double bond may additionally have one ortho-fused benzo system, each of which has from 3 up to and including 7 ring members, or lower alkyleneamino having 5 or 6 ring members or lower alkenyleneamino having one double bond and 5 ring members, each of which is interrupted in the lower alkylene or lower alkenylene moiety by an aza, lower alkylaza, oxa or thia group, and the aromatic ring A is additionally mono- or poly-substituted by lower alkyl, hydroxy-lower alkyl, halo-lower alkyl, lower alkenyl, lower alkylene bridging two adjacent carbon atoms and having 3 or 4 chain members, lower alkoxy, lower alkylthio, lower alkanesulphinyl, lower alkanesulphonyl, hydroxy, halogen, lower alkanoyloxy, lower alkanoyl and/or by nitro or, except for $R_2$, is unsubstituted, and the salts thereof.

4. Compounds according to patent claim 1 of the formula

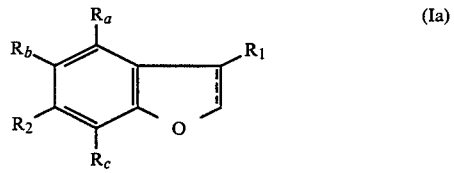

in which $R_1$ represents hydrogen or lower alkyl, $R_2$ represents, in each case 5- to 8-membered, lower alkyleneamino, lower alkenyleneamino, aza-lower alkyleneamino, N'-lower alkylaza-lower alkyleneamino, aza-lower alkenyleneamino, N'-lower alkylaza-lower alkenyleneamino, oxa- or thia-lower alkyleneamino, isoindol-2-yl, isoindolin-2-yl, indolin-1-yl or indol-1-yl, and $R_a$, $R_b$ and $R_c$ each represents, independently of the others, hydrogen, lower alkyl, hydroxy-lower alkyl, halo-lower alkyl, lower alkenyl, lower alkoxy, lower alkylthio, lower alkanesulphinyl, lower alkanesulphonyl, hydroxy, halogen, lower alkanoyloxy, lower alkanoyl or nitro, or $R_a$ together with $R_b$ represents 3- or 4-membered alkylene and $R_c$ has the meanings given above for $R_c$, and the salts thereof.

5. Compounds according to patent claim 1 of the formula Ia in which $R_1$ represents hydrogen or lower alkyl, $R_2$ represents lower alkyleneamino having 5 or 6 ring members and from 4 up to and including 10 carbon atoms, lower alkenyleneamino having one or two double bonds and 5 or 6 ring members and from 4 up to and including 10 carbon atoms or 4-oxa-lower alkyleneamino having 6 ring members and from 4 up to and including 10 carbon atoms, and $R_a$ and $R_c$ each represents hydrogen and $R_b$ represents hydrogen, lower alkyl, hydroxy-lower alkyl, halo-lower alkyl, lower alkoxy, lower alkylthio, hydroxy, halogen or lower alkanoyloxy, or $R_a$ and $R_b$ together represent lower alkylene having 3 or 4 chain members, for example having 3 or 4 carbon atoms, and $R_c$ is hydrogen, and the salts thereof.

6. Compounds according to patent claim 1 of the formula Ia in which $R_1$ represents hydrogen or lower alkyl having up to and including 4 carbon atoms, $R_2$ represents 1-pyrrolyl, 4-morpholinyl, 3-pyrrolin-1-yl or unbranched 4- or 6-membered alkyleneamino, $R_a$ and $R_c$ each represents hydrogen and $R_b$ represents hydrogen, lower alkyl having up to and including 4 carbon atoms or halogen having an atomic number of up to and including 35, or $R_c$ represents hydrogen and $R_a$ and $R_b$ together represent 3- or 4-membered alkylene or one of the radicals $R_a$ and $R_b$ represents halogen having an atomic number of up to and including 35 and the other represents lower alkyl having up to 4 carbon atoms, and the salts thereof.

7. Compounds according to patent claim 1 of the formula

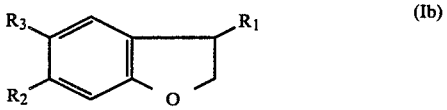

in which $R_1$ represents hydrogen or lower alkyl having up to and including 4 carbon atoms, $R_2$ represents pyrrolidin-1-yl, 1-piperidyl, pyrrol-1-yl or morpholin-4-yl and $R_3$ represents hydrogen, lower alkyl having up to and including 4 carbon atoms or halogen having an atomic number of up to and including 35, and the salts thereof.

8. Compounds according to claim 1 of the formula

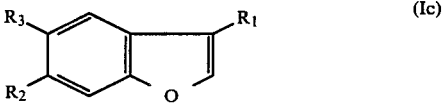

in which $R_1$ represents hydrogen or lower alkyl having up to and including 4 carbon atoms, $R_2$ represents pyrrolidin-1-yl, 1-piperidyl, pyrrol-1-yl or morpholin-4-yl and $R_3$ represents hydrogen, lower alkyl having up to and including 4 carbon atoms or halogen having an atomic number of up to and including 35, and the salts thereof.

9. Compounds according to claim 1 of the formula Ic in which $R_1$ represents hydrogen or lower alkyl having up to and including 4 carbon atoms, $R_2$ represents pyrrol-1-yl and $R_3$ represents lower alkyl having up to and including 4 carbon atoms.

10. A compound as claimed in claim 1 being 5-chloro-6-(piperidin-1-yl)-2,3-dihydrobenzofuran or a salt thereof.

11. A compound as claimed in claim 1 being 5-chloro-3-methyl-6-(piperidin-1-yl)-benzofuran a salt thereof.

12. A compound as claimed in claim 1 being 5-chloro-6-(piperidin-1-yl)-benzofuran or a salt thereof.

13. A compound as claimed in claim 1 being 5-chloro-3-methyl-6-(pyrrolidin-1-yl)-benzofuran or a salt thereof.

14. A compound as claimed in claim 1 being 3,5-dimethyl-6-(pyrrol-1-yl)-benzofuran.

15. A compound as claimed in claim 1 being 3,5-dimethyl-6-morpholinobenzofuran or a salt thereof.

16. A compound as claimed in claim 1 being 5-chloro-3-methyl-6-(pyrrol-1-yl)-benzofuran.

17. A compound as claimed in claim 1 being 3,5-dimethyl-6-morpholino-2,3-dihydrobenzofuran or a salt thereof.

18. A compound as claimed in claim 1 being 3,5-dimethyl-6-(pyrrol-1-yl)-2,3-dihydrobenzofuran.

19. A compound as claimed in claim 1 being 5-methyl-6-(pyrrol-1-yl)-benzofuran.

20. A compound as claimed in claim 1 being 5-methyl-6-(pyrrol-1-yl)-2,3-dihydrobenzofuran.

21. A pharmaceutical preparation comprising an analgesic or anti-inflammatory amount of a compound according to claim 1 and a pharmaceutically acceptable carrier.

22. A method of treating inflammation or pain conditions in warm blooded animals comprising administering a pharmaceutically effective amount of a compound according to claim 1.